(12) United States Patent
Pohl et al.

(10) Patent No.: US 11,845,769 B2
(45) Date of Patent: Dec. 19, 2023

(54) ANION EXCHANGE STATIONARY PHASES BASED ON A POLYALKYLPOLYAMINE POLYMER LAYER

(71) Applicant: DIONEX CORPORATION, Sunnyvale, CA (US)

(72) Inventors: Christopher A. Pohl, Union City, CA (US); Jinhua Chen, San Jose, CA (US)

(73) Assignee: Dionex Corporation, Sunnyvale, CA (US)

( * ) Notice: Subject to any disclaimer, the term of this patent is extended or adjusted under 35 U.S.C. 154(b) by 190 days.

(21) Appl. No.: 17/176,044

(22) Filed: Feb. 15, 2021

(65) Prior Publication Data

US 2021/0163520 A1 Jun. 3, 2021

Related U.S. Application Data

(62) Division of application No. 16/049,464, filed on Jul. 30, 2018, now abandoned.

(51) Int. Cl.
| | | |
|---|---|---|
| *C07H 1/06* | (2006.01) | |
| *B01J 41/13* | (2017.01) | |
| *B01D 15/36* | (2006.01) | |

(52) U.S. Cl.
CPC .............. *C07H 1/06* (2013.01); *B01D 15/363* (2013.01); *B01J 41/13* (2017.01)

(58) Field of Classification Search
CPC ........... C07H 1/06; B01J 41/13; B01D 15/363
USPC .................................................... 536/123.13
See application file for complete search history.

(56) References Cited

U.S. PATENT DOCUMENTS

| | | | |
|---|---|---|---|
| 5,260,205 | A | 11/1993 | Nakatani et al. |
| 6,225,129 | B1 | 5/2001 | Liu et al. |
| 6,248,798 | B1 | 6/2001 | Slingsby et al. |
| 6,682,701 | B1 | 1/2004 | Liu et al. |
| 6,783,645 | B2 | 8/2004 | Cheng et al. |
| 7,291,395 | B2 | 11/2007 | Pohl et al. |
| 7,361,273 | B2 * | 4/2008 | Heikkila ............ B01D 15/363 210/659 |
| 8,342,007 | B2 | 1/2013 | Cheng et al. |
| 8,636,885 | B2 | 1/2014 | Vana et al. |
| 8,925,374 | B2 | 1/2015 | Cheng et al. |
| 2002/0169251 | A1 * | 11/2002 | He ........................ C08F 8/00 524/599 |
| 2009/0324617 | A1 * | 12/2009 | Satomaa .......... C07K 16/3076 435/7.1 |
| 2011/0210055 | A1 | 9/2011 | Srinivasan et al. |
| 2012/0231195 | A1 | 9/2012 | Pohl et al. |

FOREIGN PATENT DOCUMENTS

| | | | |
|---|---|---|---|
| CN | 103429322 B | * | 6/2016 |
| WO | 9731864 A1 | | 9/1997 |

OTHER PUBLICATIONS

Deepak (https://lab-training.com; May 9, 2014).*
Marques et al. (FEMS Yeast Research, 16, 2016, 1-16).*
Browne et al. (Ind. Eng. Chem. Anal. Ed. 1945, 17, 10, 623, Publication Date: Oct. 1, 1945).*
Riviello; CN 103429322 B; Jun. 1, 2016 (Machine-English Translation).*
Corradini, International Journal of Carbohydrate Chemistry vol. 2012, Article ID 487564. (Year: 2012).*
Bergqvist, A., "Coating Fine Particles", Aug. 31, 2014, XP055642799, Retrieved from the Internet: URL:http://www.diva-portal.se/smash/get/diva2:759456/FULLTEXT01.pdf [retrieved on Nov. 14, 2019].
Giumanini, A.G. et al., "Facile Synthesis of N-Permethylspermine and N-Permethylspermidine from their Unmethylated Precursors", vol. 30b, 1975, pp. 820-821.
Higashihara et al. "Synthesis of Hyperbranched Polymers with Controlled Degree of Branching," Polymer Journal, vol. 44, No. 1, Oct. 19, 2011, pp. 14-29.

* cited by examiner

*Primary Examiner* — Layla D Berry

(57) ABSTRACT

An anion exchange for separating a plurality of carbohydrates includes a negatively charged substrate particle. A base polymer layer includes a first plurality of quaternary amines. The polyalkylpolyamine polymer layer is covalently attached to the base condensation polymer layer. The polyalkylpolyamine polymer layer includes a polymeric branch structure that includes a second plurality of quaternary amines. A density of the second plurality of quaternary amines increases in a direction away from the base condensation polymer layer. The anion exchange stationary phase does not have a hydroxy group spaced apart from any one of the first or the second plurality of quaternary amines by an ethyl group.

12 Claims, 19 Drawing Sheets

FIG 2
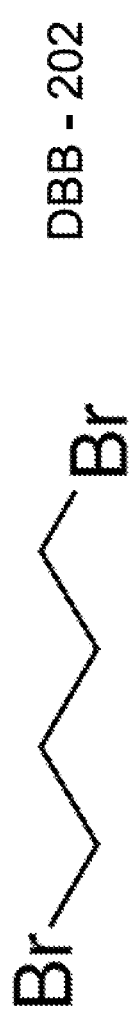
DBB - 202
206
$Br-(CH_2)_n-Br$
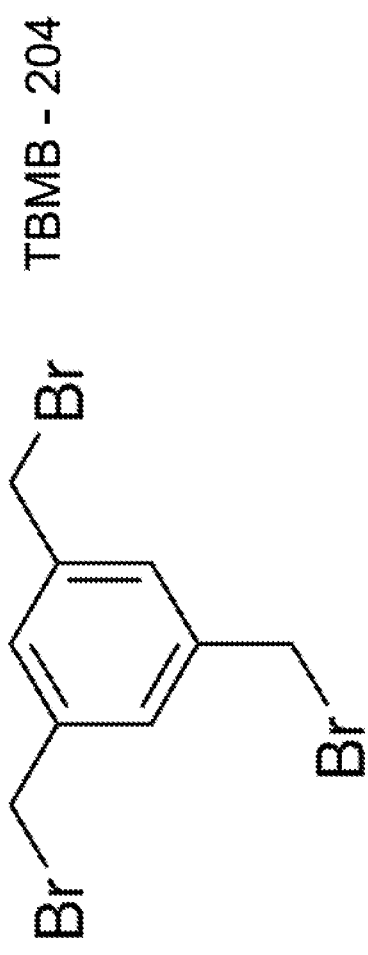
TBMB - 204

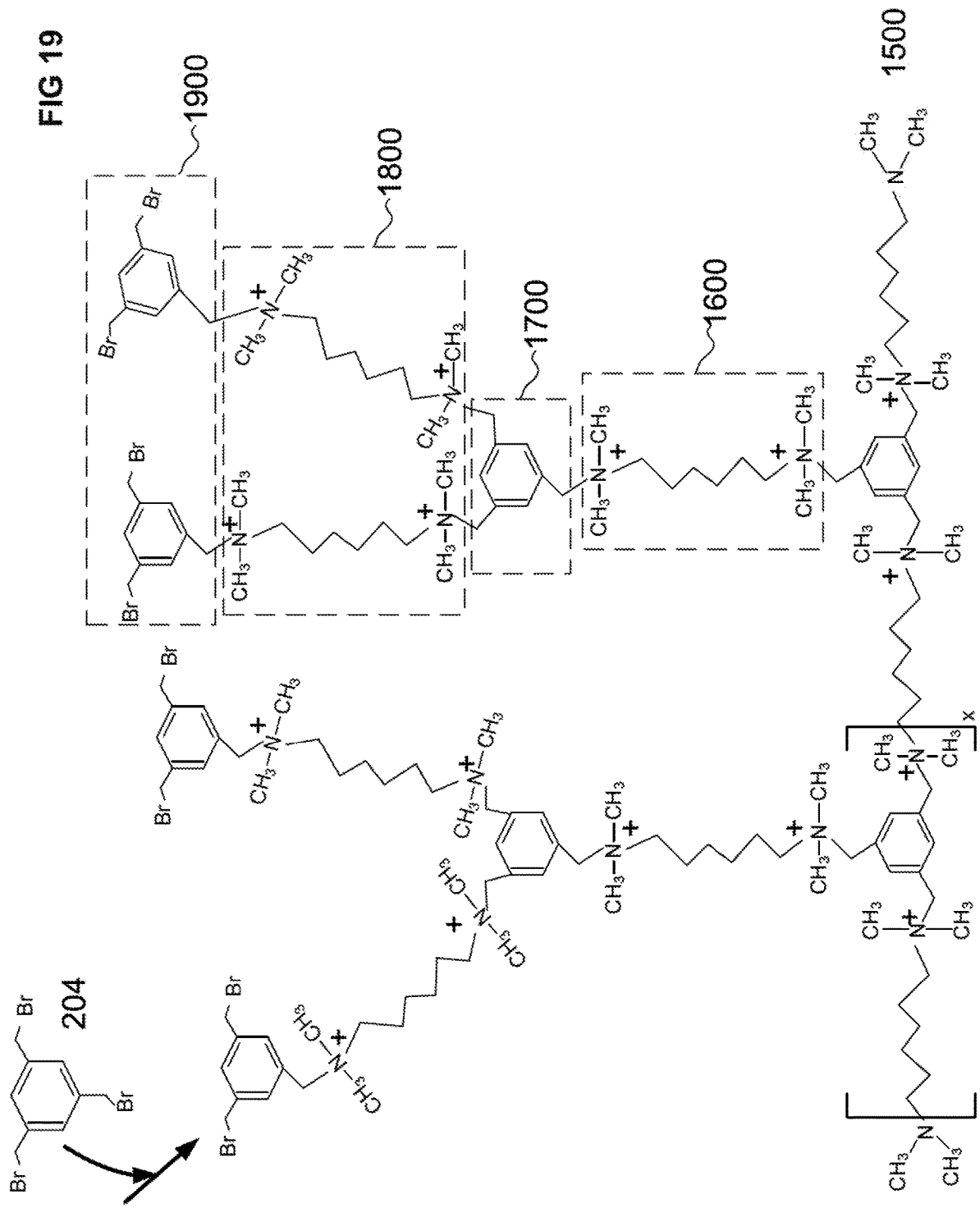

ANION EXCHANGE STATIONARY PHASES BASED ON A POLYALKYLPOLYAMINE POLYMER LAYER

CROSS REFERENCE TO RELATED APPLICATION(S)

This application is a divisional and claims the priority benefit of co-pending U.S. application Ser. No. 16/049,464, filed Jul. 30, 2018, which application is hereby incorporated herein by reference in their entireties.

FIELD OF THE INVENTION

The invention generally relates to anion exchange stationary phases based on a polyalkylpolyamine layer for applications such as chromatographically separating samples that include anions, and in particular a combination of carbohydrates, and more particularly a combination of branched glycans.

BACKGROUND

Chromatography is a widely used analytical technique for the chemical analysis and separation of molecules. Chromatography involves the separation of one or more analyte species from other matrix components present in a sample. A stationary phase of a chromatography column is typically selected so that there is an interaction with the analyte. Such interactions can be ionic, hydrophilic, hydrophobic, or combinations thereof. For example, the stationary phase can be derivatized with ionic moieties that ideally will bind to ionic analytes and matrix components with varying levels of affinity. A mobile phase is percolated through the stationary phase and competes with the analyte and matrix components for binding to the ionic moieties. The mobile phase or eluent are terms used to describe a liquid solvent or buffer solution that is pumped through a chromatography column. During this competition, the analyte and matrix components will elute off of the stationary phase as a function of time and then be subsequently detected at a detector. Examples of some typical detectors are a conductivity detector, a UV-VIS spectrophotometer, and a mass spectrometer. Over the years, chromatography has developed into a powerful analytical tool that is useful for creating a healthier, cleaner, and safer environment where complex sample mixtures can be separated and analyzed for various industries such as water quality, environmental monitoring, food analysis, pharmaceutical, and biotechnology.

U.S. Pat. No. 7,291,395 "Coated ion exchanged substrate and method of forming" described a hyperbranched anion exchange material based on a crosslinked layer that includes quaternary amine groups and hydroxy groups. In an embodiment, the anion exchange material was formed using a reaction between a diepoxide reagent and an amine group. The ring opening reaction results in a hydroxy group that is spaced apart from a quaternary amine group by a two carbon spacer. The hydroxy group produced in this type of reaction can be referred to as a beta hydroxy group with respect to a quaternary amine, which makes the hydroxy groups more acidic and in turn influences the anion binding characteristics of the anion exchange resin. During an anion exchange chromatographic separation, a hydroxide eluent is typically used. When the pH of the hydroxide eluent is sufficiently high, the beta hydroxy group can be deprotonated causing the formation of a zwitterionic ion pair with the quaternary amine, which decreases the anion binding to the quaternary amine ion exchange site. The zwitterionic ion pair has a positively charged quaternary amine that is stabilized by the negatively charged and deprotonated beta hydroxy group. The proximity of the positively charged quaternary amine and the deprotonated hydroxy group form a relatively stable zwitterionic pair that reduces the anion binding strength of the quaternary amine. Thus, the anion binding capability of anion exchange resins can be tuned based on the concentration (or pH) of the hydroxide eluent making it useful for various anion exchange chromatography tests.

However, under certain circumstances, Applicant has found that carbohydrates have little if any retention with hyperbranched anion exchange materials containing beta hydroxy groups, and thus, was not useful for this application. As such, Applicant believes that there is a need for hyperbranched anion exchange materials that do not contain beta hydroxy groups so that chromatographic analysis can be performed for carbohydrates such as branched glycans.

SUMMARY

A first embodiment of an anion exchange stationary phase for separating a plurality of carbohydrates includes a) a negatively charged substrate particle, b) a base condensation polymer layer, and c) a polyalkylpolyamine condensation polymer layer. The base condensation polymer layer is attached to the negatively charged substrate particle. The base condensation polymer layer includes a first plurality of quaternary amines, in which the first plurality of quaternary amines are spaced apart by either a first spacer or a second spacer. The base condensation polymer layer does not have a hydroxy group spaced apart from one of the first plurality of quaternary amines by an ethyl group. The polyalkylpolyamine condensation polymer layer is covalently attached to the base condensation polymer layer. The polyalkylpolyamine condensation polymer layer includes a polymeric branch structure that includes a second plurality of quaternary amines, in which the second plurality of quaternary amines are spaced apart by the first spacer or the second spacer. A density of the second plurality of quaternary amines increases in a direction away from the base condensation polymer layer. The polyalkylpolyamine condensation polymer layer does not have a hydroxy group spaced apart from one of the second plurality of quaternary amines by an ethyl group.

In regards to any of the first embodiments, the first spacer can be an alkyl, a dialkylether, a cycloalkyl, an arylalkyl, and combinations thereof.

In regards to any of the first embodiments, the second spacer can be an alkyl, a dialkylether, a cycloalkyl, an arylalkyl, and combinations thereof.

In regards to the first embodiment, which the first spacer includes a first alkyl and the second spacer includes a second alkyl, in which the first alkyl and the second alkyl are both a linear and unsubstituted alkyl.

In regards to the first embodiment, the first spacer includes a linear and unsubstituted alkyl and the second spacer includes an arylalkyl.

In regards to the first embodiment, the first spacer includes a chemical formula of $(-CH_2-)_x$ and the second spacer comprises a chemical formula of $(-CH_2-)_y$, where x and y each independently range from 3 to 10, and preferably range from 3 to 6.

A second embodiment of an anion exchange stationary phase for separating a plurality of carbohydrates is formed by a method including reacting a polyhalohydrocarbon with a polyalkylpolyamine to form a base condensation polymer layer on a negatively charged substrate particle. The base condensation polymer layer is reacted with a number of reaction cycles to form a polyalkylpolyamine condensation polymer layer. The number of reaction cycles ranges from about 3 to about 10 and each reaction cycle includes a polyhalohydrocarbon treatment and a polyalkylpolyamine treatment. After the reaction cycles, the polyalkylpolyamine condensation polymer layer is reacted with a monohaloalkane treatment. An example of a monohaloalkane is methyliodide.

In regards to the second embodiment, the negatively charged substrate particles are contained as a packed bed in a chromatography column. The reacting of the polyhalohydrocarbon with the polyalkylpolyamine includes flowing a solution of the polyhalohydrocarbon and the polyalkylpolyamine through the column to form the base condensation polymer layer on the negatively charged substrate particles.

In regards to the second embodiment, the polyhalohydrocarbon treatment includes flowing a solution of the polyhalohydrocarbon through the column. The polyalkylpolyamine treatment includes flowing a solution of the polyalkylpolyamine through the column. The monohaloalkane treatment includes flowing a solution of the monohaloalkane through the column.

In regards to any of the second embodiments, the number of reaction cycles may range from about 3 to about 4.

In regards to any of the second embodiments, the polyhalohydrocarbon can be a dihaloalkane, a dihalodialkylether, a dihalocycloalkane, a trihaloarylalkane, and a combination thereof.

In regards to any of the second embodiments, the polyalkylpolyamine can include an ether group, a cycloalkane group, an arylalkane, and a combination thereof.

In regards to any of the second embodiments, the polyalkylpolyamine can be a polyalkyltriamine, a polyalkyldiamine, and a combination thereof.

In regards to the second embodiment, all amines of the polyalkylpolyamine can be tertiary amines (e.g., polyalkylpolytertiaryamine).

In regards to the second embodiment, the polyhalohydrocarbon can be a dibromobutane, a dibromopentane, a dibromohexane, a tribromomethylbenzene, and a combination thereof.

In regards to the second embodiment, the polyalkylpolyamine can be a pentamethyldipropyltriamine, a pentamethyldihexylltriamine, a permethylated spermine, a permethylated spermidine, and a combination thereof.

In regards to the second embodiment, the polyhalohydrocarbon is dibromobutane and the polyalkylpolyamine is pentamethyldihexylltriamine.

In regards to the second embodiment, the polyhalohydrocarbon is a trihaloalkylaryl and the polyalkylpolyamine is an alkyldiamine.

In regards to the second embodiment, the polyhalohydrocarbon is tribromomethylbenzene and the polyalkylpolyamine is tetramethylhexanediamine.

A third embodiment of an anion exchange stationary phase for separating a plurality of carbohydrates includes A) a negatively charged substrate particle, B) a base condensation polymer layer 300, C) a first alkyl condensation reaction product (CRP) 400, D) a first polyalkylpolyamine CRP 500, E) a second alkyl CRP 600, F) a second alkyl CRP 700, G) a third alkyl CRP, and H) a third alkyl CRP. The base condensation polymer layer 300 is attached to the negatively charged substrate particle. The base condensation polymer layer includes a reaction product of i) a first polyhalohydrocarbon, and ii) a first polyalkylpolyamine. The first alkyl CRP 400 is covalently attached to the base condensation polymer layer 300. The first alkyl CRP 400 includes a reaction product of i) an amine group of the base condensation polymer layer 300, and ii) a second polyhalohydrocarbon. The amine group of the base condensation polymer layer 300 includes a positive charge so that the base condensation polymer layer is ionically coupled to the negatively charged substrate particle. The first polyalkylpolyamine CRP 500 is covalently attached to the first alkyl CRP 400. The first polyalkylpolyamine CRP 500 includes a reaction product of i) a halide group of the second polyhalohydrocarbon, and ii) a second polyalkylpolyamine. The second alkyl CRP 600 is covalently attached to the first polyalkylpolyamine CRP 500. The second alkyl CRP 600 includes a reaction product of i) an amine group of the first polyalkylpolyamine CRP 500 and ii) a third polyhalohydrocarbon. The second polyalkylpolyamine CRP 700 is covalently attached to the second alkyl CRP 600. The second polyalkylpolyamine CRP 700 includes a reaction product of i) a halide group of the third polyhalohydrocarbon, and ii) a third polyalkylpolyamine. The third alkyl CRP is covalently attached to the second polyalkylpolyamine CRP 700. The third alkyl CRP includes a reaction product of i) an amine group of the second polyalkylpolyamine CRP and ii) a fourth polyhalohydrocarbon. The third polyalkylpolyamine CRP is covalently attached to the third alkyl CRP. The third polyalkylpolyamine CRP includes a reaction product of i) a halide group of the fourth polyhalohydrocarbon, and ii) a fourth polyalkylpolyamine.

In regards to the third embodiment, the first polyhalohydrocarbon, second polyhalohydrocarbon, third polyhalohydrocarbon, and fourth polyhalohydrocarbon can include a dihaloalkane. The first polyalkylpolyamine, second polyalkylpolyamine, third polyalkylpolyamine, and fourth polyalkylpolyamine can include a polyalkyltriamine.

A fourth embodiment of an anion exchange stationary phase for separating a plurality of carbohydrates includes A) a negatively charged substrate particle, B) a base condensation polymer layer 1500, C) a first polyalkylpolyamine CRP 1600, D) a first polyalkylaryl CRP 1700, E) a second polyalkylpolyamine CRP 1800, F) a second polyalkylaryl CRP 1900, G) a third polyalkylpolyamine CRP, and H) a third polyalkylaryl CRP. The base condensation polymer layer 1500 is attached to the negatively charged substrate particle. The base condensation polymer layer includes a reaction product of i) a first polyhalohydrocarbon, and ii) a first polyalkylpolyamine. The amine group of the base condensation polymer layer 1500 includes a positive charge so that the base condensation polymer layer is ionically coupled to the negatively charged substrate particle. The first polyalkylpolyamine condensation reaction product 1600 is covalently attached to the base condensation polymer layer 1500. The first polyalkylpolyamine condensation reaction product 1600 includes a reaction product of i) a halide group of the base condensation polymer layer 1500, and ii) a second polyalkylpolyamine. The first polyalkylaryl condensation reaction product 1700 is covalently attached to the first polyalkylpolyamine condensation reaction product 1600. The first polyalkylaryl condensation reaction product 1700 includes a reaction product of i) an amine group of the first polyalkylpolyamine condensation reaction product 1600, and ii) a second polyhalohydrocarbon. The second polyalkylpolyamine condensation reaction product 1800 is covalently attached to the first polyalkylaryl condensation reaction product 1700. The second polyalkylpolyamine condensation reaction product 1800 includes a reaction product of i) a halide group of the first polyalkylaryl condensation reaction product 1700, and ii) a third polyalkylpolyamine. The second polyalkylaryl CRP 1900 is covalently attached to the second polyalkylpolyamine CRP 1800. The second polyalkylaryl CRP 1900 includes a reaction product of i) an amine group of the second polyalkylpolyamine CRP 1800, and ii) a third polyhalohydrocarbon. The third polyalkylpolyamine CRP is covalently attached to the second polyalkylaryl CRP 1900. The third polyalkylpolyamine CRP includes a reaction product of i) a halide group of the second polyalkylaryl CRP 1900, and ii) a fourth polyalkylpolyamine. The third polyalkylaryl CRP is covalently attached to the third polyalkylpolyamine CRP. The third polyalkylaryl CRP includes a reaction product of i) an amine group of the third polyalkylpolyamine, and ii) a fourth polyhalohydrocarbon.

In regards to the fourth embodiment, it may further includes a reaction product of i) a halide group of the third polylalkylaryl CRP, and ii) a tertiary amine.

In regards to the fourth embodiment, the first polyhalohydrocarbon, second polyhalohydrocarbon, third polyhalohydrocarbon, and fourth polyhalohydrocarbon can include a trihaloalkylaryl, and the first polyalkylpolyamine, second polyalkylpolyamine, third polyalkylpolyamine, and fourth polyalkylpolyamine can include a polyalkyldiamine.

A fifth embodiment is a method of using an anion exchange stationary phase for separating a plurality of carbohydrates in a sample with the anion exchange stationary phase of any of the first, second, and third embodiments. The method includes flowing an eluent through a chromatography column containing the anion exchange stationary phase. The eluent includes a hydroxide. A sample is injected that includes a plurality of carbohydrates into the chromatography column. At least one carbohydrate is separated from the sample injected into the chromatography column. The at least one carbohydrate is detected at a detector.

In regards to the fifth embodiment, the at least one carbohydrate is a branched glycan.

In regards to the above embodiments, the negatively charged substrate particle can include a crosslinked divinylbenzene and ethylvinyl benzene copolymer, in which at least a surface of the negatively charged substrate particle includes sulfonate groups.

In regards to the above embodiments, the negatively charged substrate particle comprises a crosslinked divinylbenzene and ethylvinyl benzene copolymer, in which at least a surface of the negatively charged substrate particle includes carboxylate groups.

In regards to the above embodiments, in which the base condensation polymer layer is positively charged and ionically attached to the negatively charged substrate particle.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 2 illustrates various chemical structures of polyhalohydrocarbon reagents that can be used in forming polymers and reaction products for anion exchange resins.

FIG. 19 illustrates a schematic of a second polyalkylaryl that is covalently attached to the second polyalkylpolyamine reaction product. The second polyalkylaryl reaction product is a reaction product of the pendant tertiary amine groups of the third TMHDA and a halide group of a third TBMB.

DETAILED DESCRIPTION OF EMBODIMENTS

Figure 1:
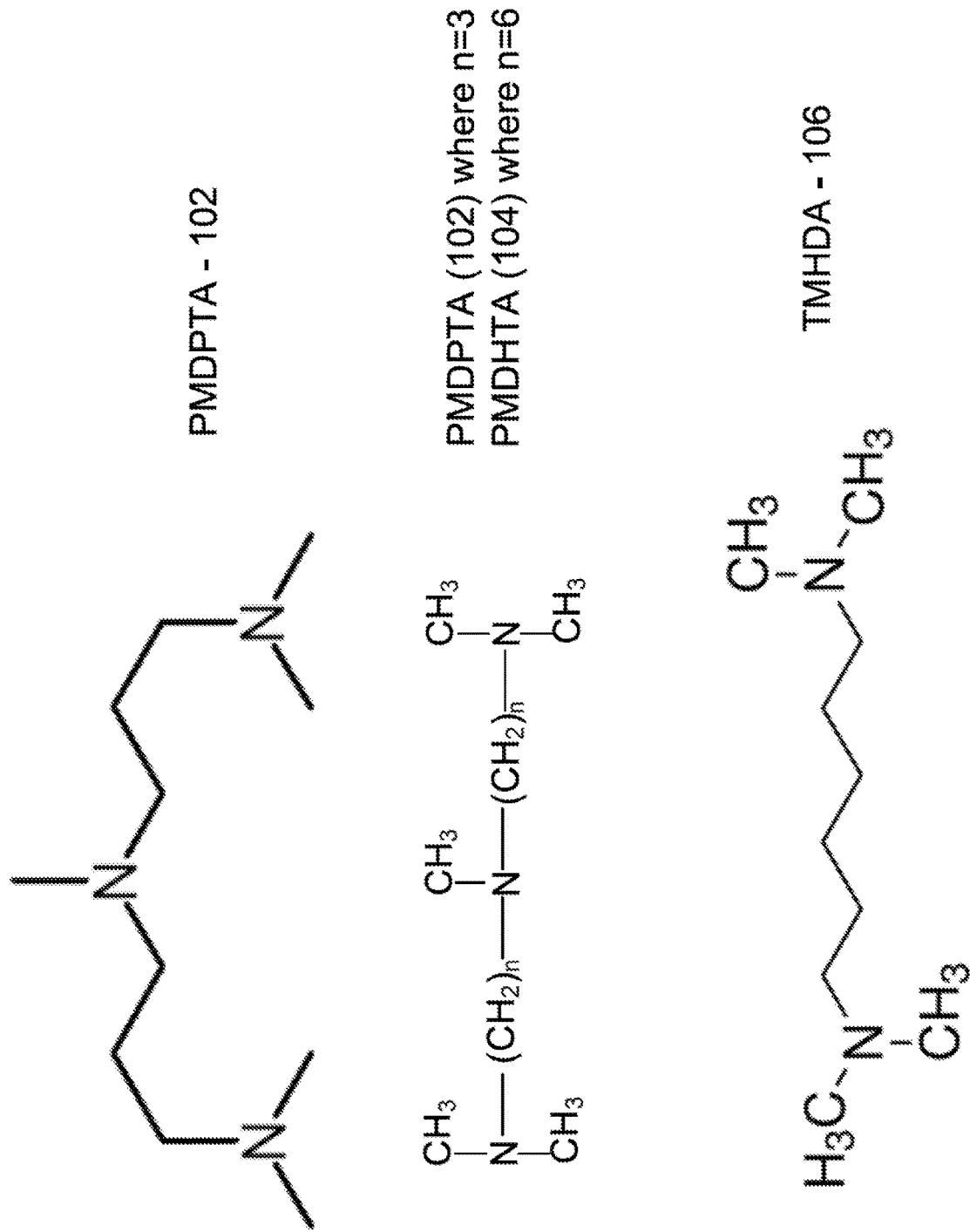
FIG. 1 illustrates various chemical structures of polyalkylpolyamine reagents that can be used in forming polymers and reaction products for anion exchange resins.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

Herein the term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl (e.g., —$CH_2$—$CH_2$—$CH_3$, —$CH_2$—$CH_2$—$CH_2$—), isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl". Alkyl groups that are limited to hydrocarbon groups are termed "homoalkyl". The term "alkyl" can also mean "alkylene" or "alkyldiyl" as well as alkylidene in those cases where the alkyl group is a divalent radical.

Herein the term "alkylene" or "alkyldiyl" by itself or as part of another substituent means a divalent radical derived from an alkyl group, as exemplified, but not limited, by —$CH_2CH_2CH_2$— (propylene or propane-1,3-diyl), and further includes those groups described below as "heteroalkylene". Typically, an alkyl (or alkylene) group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl", "lower alkylene" or "lower alkyldiyl" is a shorter chain alkyl, alkylene or alkyldiyl group, generally having about 10 or fewer carbon atoms, about 8 or fewer carbon atoms, about 6 or fewer carbon atoms or about 4 or fewer carbon atoms.

Herein the term "alkylidene" by itself or as part of another substituent means a divalent radical derived from an alkyl group, as exemplified, but not limited, by $CH_3CH_2CH_2$= (propylidene). Typically, an alkylidene group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl" or "lower alkylidene" is a shorter chain alkyl or alkylidene group, generally having about 10 or fewer carbon atoms, about 8 or fewer carbon atoms, about 6 or fewer carbon atoms or about 4 or fewer carbon atoms.

Herein the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Herein the term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S and B, and wherein the nitrogen and sulfur atoms may optionally be oxidized and the nitrogen heteroatom may optionally be quaternized. The heteroatom(s) O, N, B, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—$NHCH_3$, —$CH_2$—$CH_2$—$N(CH_3)$—$CH_3$, —$CH_2$—S—$CH_2$—$CH_3$, —$CH_2$—$CH_2$, —S(O)—$CH_3$, —$CH_2$—$CH_2$—S(O)2-$CH_3$, —CH=CH—O—$CH_3$, —$Si(CH_3)_3$, —$CH_2$—CH=N—$OCH_3$, and —CH=CH—$N(CH_3)$—$CH_3$. Up to two heteroatoms may be consecutive, such as, for example, —$CH_2$—NH—$OCH_3$ and —$CH_2$—O—$Si(CH_3)_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Optionally, for alkylene and heteroalkylene linking groups, no orientation of the linking group is implied by the direction in which the formula of the linking group is written. For example, the formula —$CO_2R'$— optionally represents both —C(O)OR' and —OC(O)R'.

Herein the terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Herein the terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

Herein the term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, herein the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR"C(O)NR"R"', —NR"C(O)$_2$R', —NR—C(NR'R"R"')=NR"", —NR—C(NR'R")=NR"', —S(O)R', —S(O)$_2$R', —OS(O)$_2$R', —S(O)$_2$NR'R", —NRSO2R', —CN and —$NO_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1 -3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro ($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

A combination of multi-halogen reagents and multi-amine reagents are described that produce hyperbranched polymers containing no beta hydroxy groups. A hyperbranched anion exchange polymer has a structure that has an increasing number of branches as the polymer layer extends outwardly from the substrate. The increasing number of branches causes an increasing density of anion exchange sites towards the outer portion of the hyperbranched structure. A wide variety of different capacities and selectivities for hyperbranched structure can be achieved using various combinations of reagents, reagent concentrations, and the number of reaction cycles. For instance, hyperbranched anion exchange structures can be generated with a high ion exchange capacity and high stationary phase pH. Hyperbranched anion exchange structure have a structure similar to highly branched glycans derived from glycoproteins, and thus, hyperbranched anion exchange structures are suitable for separating highly branched glycans by providing selectivity without unduly restricting mass transport. The anion exchange stationary phase may be referred to as a resin.

Glycans include a large number of carbohydrates linked to a glycoprotein. A glycan may include saccharide subunits such as glucose, galactose, fructose, mannose, galactosamine, and glucosamine. It is believed that the pKa of beta hydroxy groups have a pKa of about 13.9, which is close to the pKa's of the saccharide subunits that are attached to glycans. Thus, pH values that cause portions of a glycan to be ionized (as an anion) can also cause beta hydroxy groups to be ionized resulting in low retention at the anion exchange resin.

In an embodiment, hyperbranched polymers can be formed from dihaloalkyls and permethylated triamines. Exemplary reagents, pentamethyldipropylenetriamine 102 and 1,4-dibromobutane 202 can be used to produce a hyperbranched polymer, as illustrated in FIGS. 1 and 2, respectively. Initially, these the two reagents together in a 1:1 mole ratio to form a ground layer on a surface sulfonated super macroporous resin, and then alternate reactions with 1,4-dibromobutane followed by reaction with pentamethyldipropylenetriamine to produce a hyperbranched anion exchange polymer that is free from having any beta hydroxy groups. It should be noted that dihaloalkane is water-insoluble, and thus, an organic solvent was used to dissolve the dihaloalkanes for reacting with a permethylated triamine. A reaction product of the dihaloalkanes and the permethylated triamine is a halide salt, which tends to precipitate in organic solvents and causes the reaction to terminate. The halide salt is more soluble in polar solvents. However, the use of polar solvents tend to excessively reduce the reaction rate making it difficult to produce suitable molecular weight polymers. Thus, to prepare the ground layer, it is necessary to react the two reagents in a solvent (or solvent mixture) that balances all of these requirements of being able to dissolve the reactants, reaction products, and have a suitable reaction rate to reach the desired polymer molecular weight. In an embodiment, a solvent mixture having a minimum amount of methanol necessary to keep the polymer in solution with acetonitrile (e.g., 4 parts acetonitrile to 1 part methanol) allows for the preparation of suitable polymers.

Applicant believes that the charge density of the quaternary ion exchange sites in a hyperbranched structure can be too high, which would result in excessive stress on the bonds between the two ion exchange sites. In an embodiment, Applicant believes that a spacer length between pairs of quaternary amine groups can be about greater than or equal to a propyl group so that the ion exchange site density is not too high. However, if the spacer is group is too long, then the ion exchange site density can be too low for effectively separating anions and providing a sufficiently high ion exchange capacity.

In another embodiment, the permethylated amines such as pentamethyldibutylenetriamine or pentamethyldihexamethylenetriamine may be used in conjunction with 1,4-dibromobutane. This would allow positioning of the quaternary amine ion exchange sites to be spaced apart by either a butyl or hexyl group. The permethylated amine reagent can be in the form of tritertiary amines where the alkylation by 1,4-dibromobutane results in the liberation of a bromide ion that can ionically associate with the formed quaternary amine. These reagents will also allow the formation of hyperbranched polymers free from any beta hydroxy groups.

In another embodiment, permethylated diamines may be used in conjunction with 1,3,5-tribromomethylbenzene to create hyperbranched structures. Examples of permethylated diamines are tetramethyl-1,4-butanediamine or tetramethyl-1,6-hexanediamine 106. These reagents will also allow the formation of hyperbranched polymers free from any beta hydroxy groups.

In an embodiment, a series of condensation reaction products or polymer layers can be formed on a substrate. A polymer formed in a polymerization reaction with a polyalkylpolyamine and a polyhalohydrocarbon may be referred to as a condensation polymer or a condensation polymer reaction product or a condensation polymer layer. Similarly, a condensation reaction product CRP can be a product from a condensation reaction between a polymer and a reagent such as an alkylhalide or amine based reagent chemical, which results in a loss of a halide or a halide and a hydrogen. It should be noted that the reaction of an alkylhalide and a tertiary amine based reagent results in a loss of a halide and does not generate the loss of hydrogen. The reaction of an alkylhalide and a primary or secondary amine based reagent results in a loss of a halide and a hydrogen, where the generated hydrogen may interfere in polymerization processes.

A polyalkylpolyamine can be a polyalkyltriamine or a polyalkyldiamine. FIG. 1 illustrates polyalkyltriamine in the form of 2,6,10-trimethyl-2,6,10-triazaundecane (pentamethyldipropyltriamine, PMDPTA 102) and 2,9,13-Trimethyl-2,9,13-triazaheptadecane (pentamethyldihexyltriamine, PMDHTA 104). Referring to FIG. 1, the alkyl spacer for polyalkyltriamine can have an n value that ranges from about 3 to about 10, and preferably from about 3 to about 6. FIG. 1 also illustrates a polyalkyldiamine in the form of N,N,N',N'-tetramethyl-1,6-hexanediamine TMHDA 106.

A polyalkylpolyamine may be a reagent compound that include two or more alkyl groups and two or more amine groups. In an embodiment, the polyalkylpolyamine may have a portion or all of the amine groups be alkylated. The alkylated amine groups of the polyalkylpolyamine may have a portion or all of the amine groups be tertiary amines. Although FIG. 1 only illustrates polyalkylpolyamine reagents that have alkyls attached to the amines, a portion or all of the alkyls can be an alkylether, cycloalkyl, arylalkyl, and combinations thereof. In an embodiment, the alkanes attached in between two amine groups (i.e., spacer) can have a length of 3 to 10 atoms, and preferably have a length of 3 to 6 atoms.

A polyhalohydrocarbon can be a polyhaloalkane or a polyhaloalkylaryl. The polyhaloalkane can be a dihaloalkane such as 1-4-dibromobutane DBB 202, as illustrated in FIG. 2. The polyhaloalkylaryl can be a trihaloalkylaryl such as 1,3,5-tri(bromomethyl)benzene TBMB 204, as illustrated in FIG. 2. In an embodiment, a dihaloalkane can be represented by a chemical formula 206 as illustrated in FIG. 2. The value n as it relates to chemical formula 206 can range from 3 to 10, and preferably range from 3 to 6.

A polyhalohydrocarbon may be a reagent compound that include two or more halide groups attached to a hydrocarbon. The halide group can be a bromide or iodide group. The polyhalohydrocarbon may have 2 to 10 halide groups, and preferably 2 to 3 halide groups. In an embodiment, the spacer between two halide groups of a polyhalohydrocarbon can have a length of 3 to 10 atoms, and preferably have a length of 3 to 6 atoms. The hydrocarbon portion (spacer) of the polyhalohydrocarbon in between a pair of halide groups may include an alkyl, a cycloalkyl, an arylalkyl, a dialkyl ether group, and combinations thereof.

Figure 3:
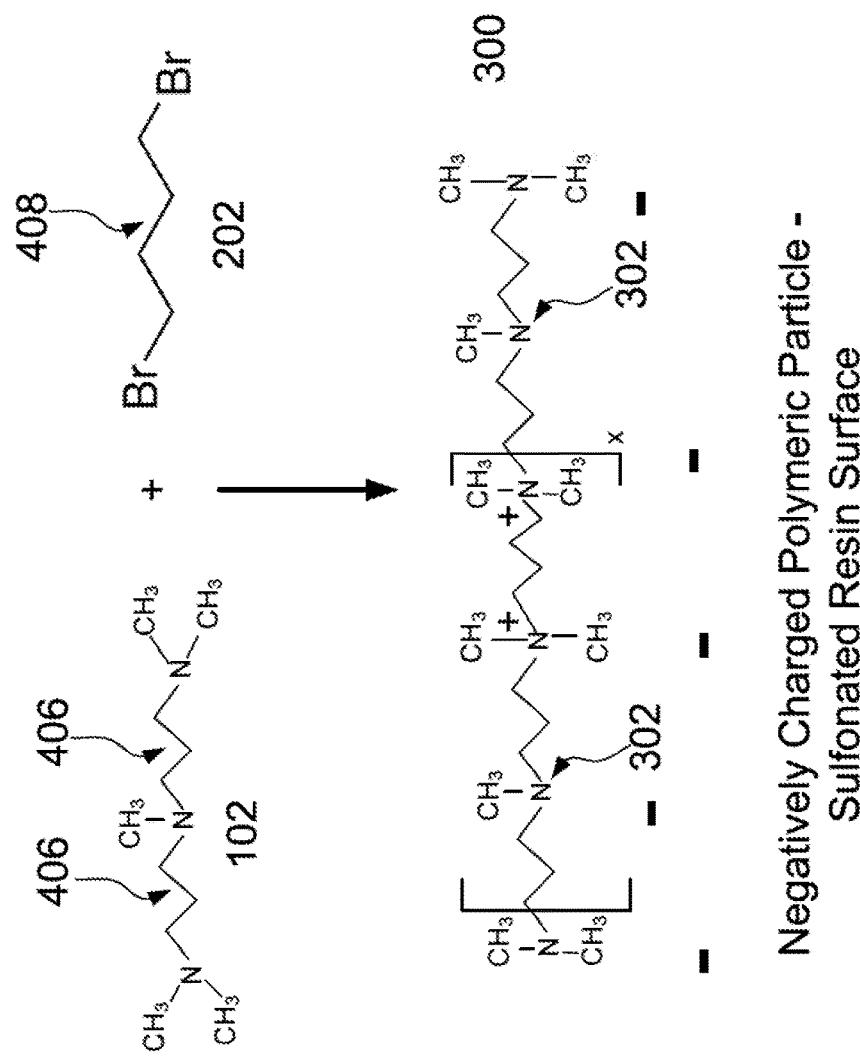
FIG. 3 illustrates a schematic of a base polymer layer formed from a first polyakyltriamine and a first dihaloalkane where the base polymer layer is attached to a negatively charged substrate particle.

FIG. 3 illustrates a schematic representation of a base condensation polymer layer 300 formed from a reaction with a first PMDPTA 102 and a first DBB 202 where the base polymer layer 300 is attached to a negatively charged substrate particle. The negatively charged substrate particle can be contained as a packed bed in a chromatography column. A solution of the PMDPTA 102 and dihaloalkane 202 can be flowed through the column to form the base condensation polymer layer on the negatively charged substrate particle. It is worthwhile to note that the base condensation polymer layer 300 does not have beta hydroxy groups since no epoxide reagents were employed. As illustrated in FIG. 3, the base condensation polymer layer 300 includes quaternary amines and tertiary amines. In an aspect, a mole ratio can be a 1:1 mole ratio of PMDPTA 102 and DBB 304 to form the base polymer layer. Although the base polymer layer 300 is depicted as linear (by reacting only the terminal end amines of PMDPTA 102), as illustrated in FIG. 3, it is possible for some of the middle amine groups (e.g, 302) to be quaternized and form either a branched or crosslinked portion. The base layer 300 can be formed in the presence of a negatively charged polymeric particle where the base layer associates and/or partially binds with the negatively charged polymeric particle, as illustrated in FIG. 3. For simplicity, the bromide salt associated with quaternary amine is not shown in the figures. The term x in FIG. 3 may range from about 5 to about 150.

The negatively charged polymeric particle can be any inert polymeric substrate particle that is chemically stable under the intended conditions of use (e.g., pH 0 to 14). The polymeric particle may be based on a divinylbenzene (DVB) crosslinking monomer and a support resin monomer where the support resin monomer may be an ethylvinylbenzene (EVB) monomer, a styrene monomer, and a combination thereof. The mole percent of DVB can be 55% and EVB can be 45%. The support resin particles may have a diameter ranging from about 1 micron to about 20 microns, preferably from about 2 microns to about 10 microns, and more preferably from about 3 microns to about 7 microns. The support resin particles may have a surface area ranging from about 20 $m^2/g$ to about 800 $m^2/g$, preferably from about 20 $m^2/g$ to about 500 $m^2/g$, more preferably from about 20 $m^2/g$ to about 100 $m^2/g$, and yet more preferably be about 20 $m^2/g$ to about 30 $m^2/g$. The support resin particles may have a pore size ranging from about 1000 angstroms to about 2000 angstroms.

In some embodiments, the negatively charged substrate particle may include one or more super macroporous particles (SMP). SMP can be obtained from commercial sources, including Agilent PLRP-s1000A and Waters Styragel HR4-HR6. The super macroporous particle can have a diameter of 4-6 μm, a surface area of 20-30 $m^2/g$, pore sizes of 1000 Å-2000 Å, and a crosslinking mole ratio of 55% of the divinylbenzene and a mole ratio of 45% of the ethylvinylbenzene.

Alternatively, the polymeric particles may be based on other vinylaromatic monomers such as alpha-methylstyrene, chlorostyrene, chloromethylstyrene, vinyltoluene, vinylnaphthalene, and a combination thereof. The polymeric particles may also be based on unsaturated monomers, and copolymers of the above vinylaromatic monomers and unsaturated monomers. Preferably such monomers will be copolymerized with a vinylaromatic crosslinking monomer such as divinylbenzene but other vinylaromatic crosslinking monomers such as trivinylbenzene, divinylnaphthalene, and a combination thereof may also be used.

The polymeric particles can be sulfonated to create a negative charge at least on the surface of the particle. For example, particles made with 55% DVB and 45% EVB can be sulfonated by treating the particles with glacial acetic acid and concentrated sulfuric acid.

Base layer 300 can be reacted with a number of reactions cycles of reagents to form a polyalkylpolyamine condensation polymer layer. In an embodiment, the number of reaction cycles may range from 1 to 10, preferably 3 to 10, and more preferably 3 to 6. Each reaction cycle includes a) a dihaloalkane treatment and b) a polyalkyltriamine treatment. After performing the number of reaction cycles, the polyalkylpolyamine condensation polymer layer may be reacted with a monohaloalkane treatment to alkylate any residual tertiary amines.

Figure 4:
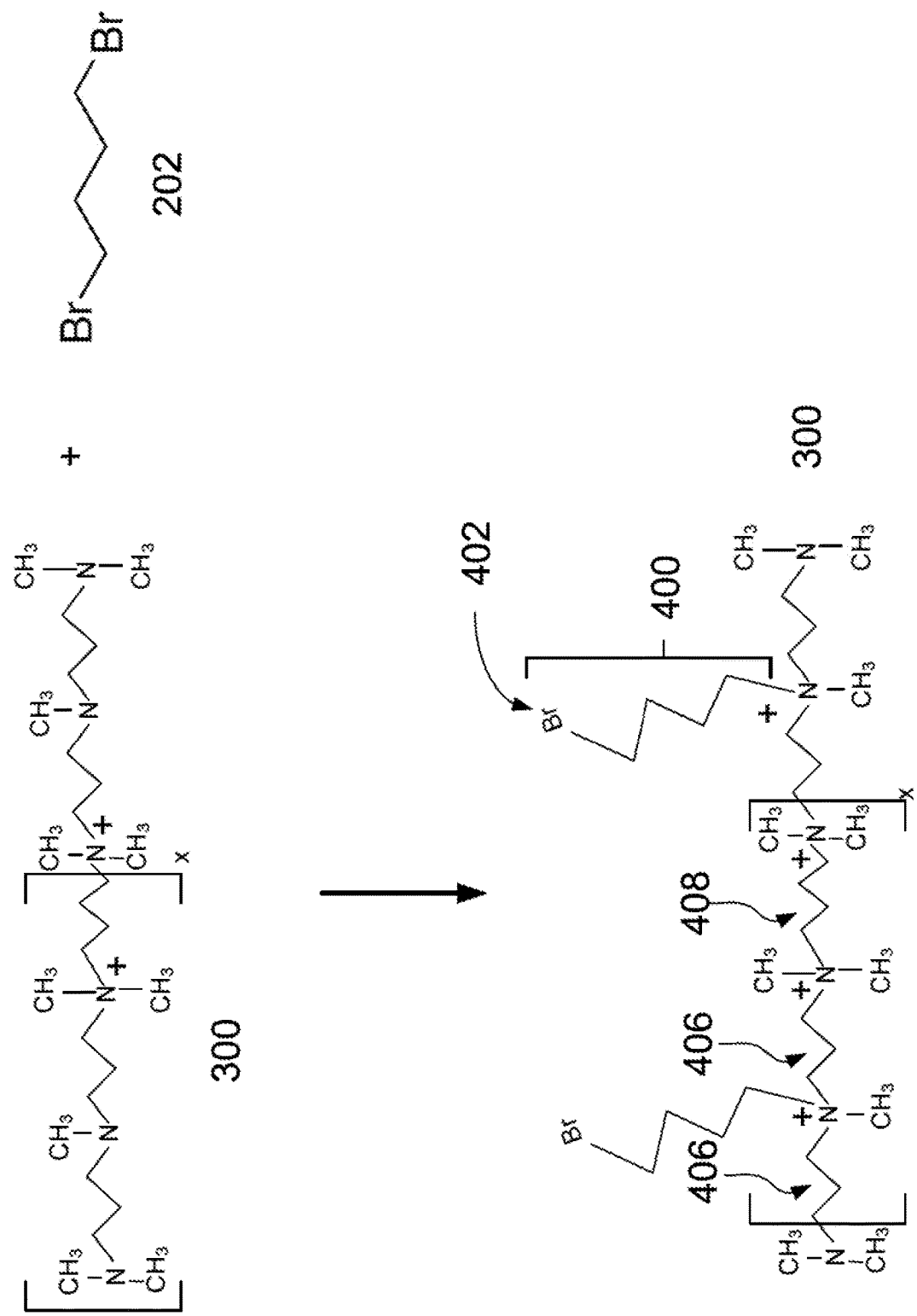
FIG. 4 illustrates a schematic of a first alkyl reaction product that has pendant halide groups and is covalently attached to the base polymer. The first alkyl reaction product is a reaction product of an amine group of the base polymer and a second dihaloalkane.

For the first step a) of a first cycle, a second DBB 202 can be reacted with a tertiary amine of base layer 300 to form a first alkyl condensation reaction product (CRP) 400 having pendant halide groups 402, as illustrated in FIG. 4. In addition, at least a portion of the tertiary amines 302 of base layer 300 are alkylated to form quaternary amines that have a positive charge. It is worthwhile to note that positive charges from the quaternary amines are believed to help base layer 300 to ionically bond to the negatively charged particles. The quaternary amines of the base condensation polymer layer 300 are spaced apart by either a first spacer 406 or a second spacer 408. The first spacer 406 is derived from PMDPTA 102 and the second spacer 408 is derived from DBB 202, as shown in FIGS. 3 and 4.

Figure 5:
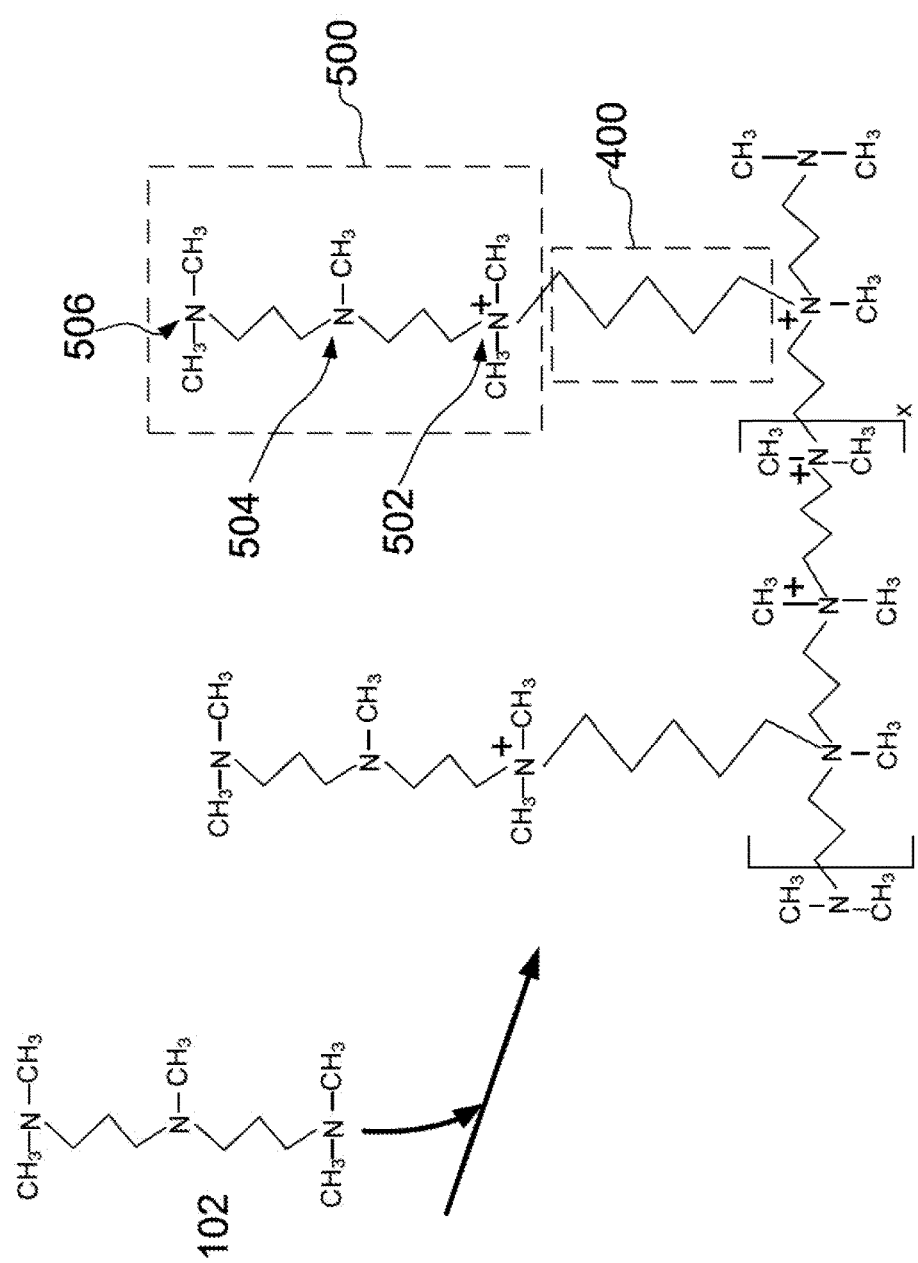
FIG. 5 illustrates a schematic of a first polyalkylpolyamine reaction product that is covalently attached to the first alkyl reaction product. The first polyalkylpolyamine reaction product is a reaction product of the pendant halide group of the second dihaloalkane and an amine group of a second polyalkyltriamine.

For a second step b) of the first cycle, the pendant halide groups 402 of the first alkyl CRP 400 can be reacted with a second PMDPTA (a second polyalkyltriamine) to form a first polyalkylpolyamine CRP 500, as illustrated in FIG. 5. The first polyalkylpolyamine CRP 500 is covalently attached to the first alkyl CRP 400. Each branch of the first polyalkylpolyamine CRP 500 includes a quaternary amine 502 and two tertiary amines 504 and 506, as illustrated in FIG. 5. Although FIG. 5 illustrates PMDPTA as only reacting with only one terminal amine group 502, it is possible for some of the PMDPTA compounds to crosslink by reacting two or three of the amine groups with the halide groups of the first alkyl CRP 400. In addition, it is possible for only the middle amine group 504 of the PMDPTA to react with a halide group of the first alkyl CRP 400.

Figure 6:
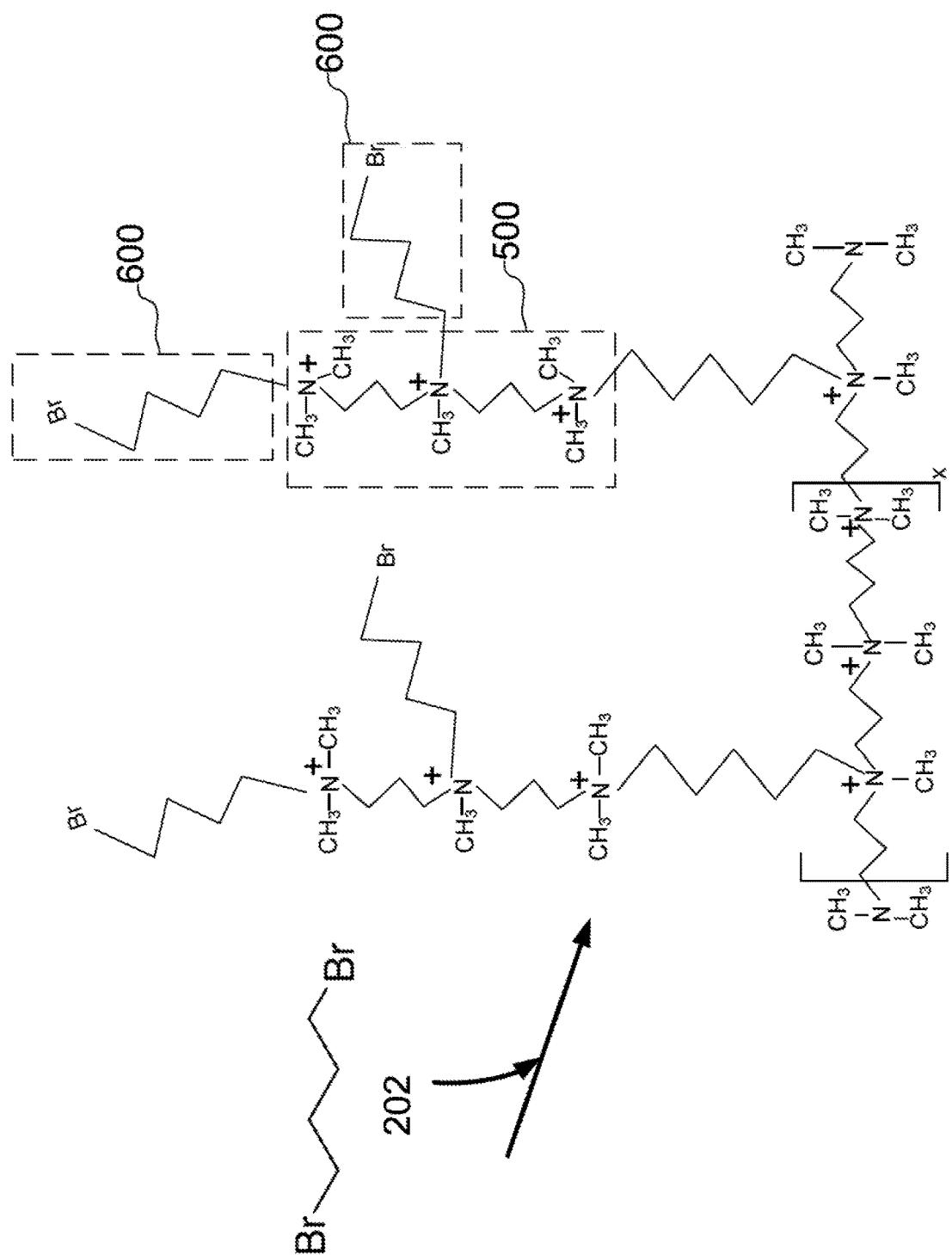
FIG. 6 illustrates a schematic of a second alkyl reaction product that has a pendant halide group and is covalently attached to the first polyalkylpolyamine reaction product. The second alkyl reaction product is a reaction product of an amine group of the first polyalkylpolyamine reaction product and a third dihaloalkane.

Now that one reaction cycle of two steps has been performed, a second cycle of two steps may be performed to create a hyperbranched structure. For a first step a) of a second cycle, the two tertiary amines 504 and 506 of the first polyalkylpolyamine CRP 500 can each be reacted with two dihaloalkanes (third DBB) to form a second alkyl condensation reaction product 600, as illustrated in FIG. 6. The second alkyl CRP 600 is covalently attached to the first polyalkylpolyamine CRP 500.

Although FIG. 6 illustrates each dihaloalkane compound as only reacting with only one halide group (of the two halide groups), it is possible for a some of the dihaloalkane compounds to crosslink by reacting both of two halide groups with the first polyalkylpolyamine CRP 500, or one halide group of the dihaloalkane with one portion of the first polyalkylpolyamine CRP 500 and the other halide group of the same dihaloalkane with another portion of the first polyalkylpolyamine CRP 500.

Figure 7:
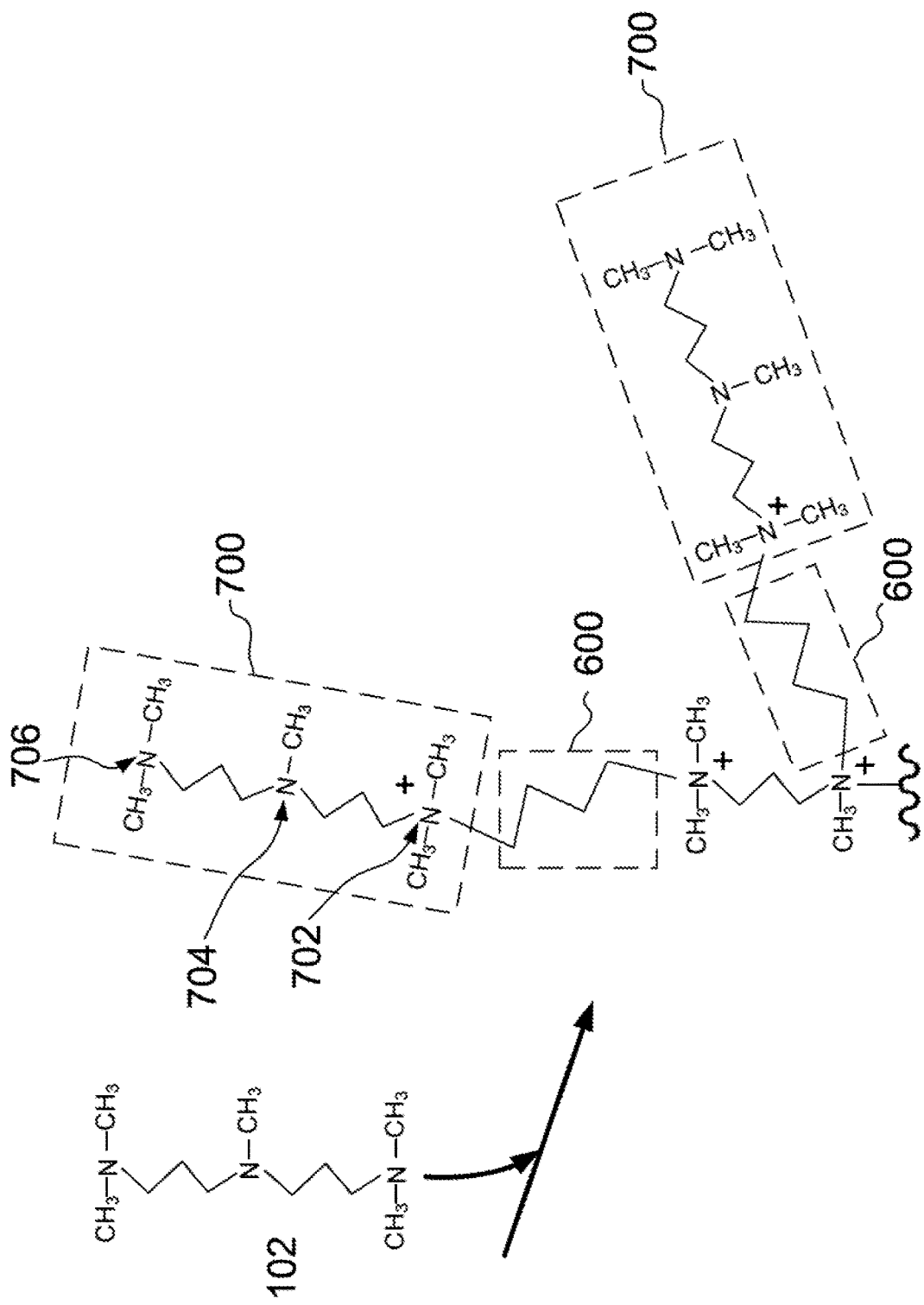
FIG. 7 illustrates a schematic of a second polyalkylpolyamine that is covalently attached to the second alkyl reaction product. The second polyalkylpolyamine reaction product is a reaction product of the pendant halide group of the third dihaloalkane and an amine group of a third polyalkyltriamine.

For a second step b) of the second cycle, the pendant halide groups of the second alkyl CRP 600 can then be reacted with a third PMDPTA to form a second polyalkypolyamine CRP 700 that has a quaternary amine 702 and two tertiary amines 704 and 706, as illustrated in FIG. 7. The second polyalkylpolyamine CRP 700 is covalently attached to the second alkyl CRP 600.

A third reaction cycle of two steps can be performed with the second polyalkypolyamine CRP 700. For a first step a) of a third cycle, the two tertiary amines 704 and 706 of first polyalkypolyamine CRP 700 can each be reacted with two dihaloalkanes (fourth DBB) to form a third alkyl CRP (not shown). It should be noted that the structure of the third alkyl CRP is analogous to the structure of the second alkyl CRP 600.

For a second step b) of the third cycle, the pendant halide groups of the third alkyl CRP can then be reacted with a fourth PMDPTA to form a third polyalkypolyamine CRP that has two tertiary amines (not shown). It should be noted that the structure of the third polyalkypolyamine CRP is analogous to the structure of the second polyalkypolyamine CRP 700.

In an embodiment, more than 3 cycles may be performed by repeating steps a) and b). It should be noted that the reaction using PMDPTA, as illustrated in FIGS. 3 to 7, can be modified by substituting PMDPTA with PMDHTA. The anion exchange stationary phases using PMDPTA has a higher density of anion exchange sites than anion exchange stationary phases using PMDHTA because of the increased length of the spacer chain from C3 to C6. It should also be noted that FIGS. 3 to 7 are exemplary and that PMDPTA may be substituted with other polyalkylpolyamines described herein and that DBB may also be substituted with other polyhalogenhydrocarbons described herein.

Figure 15:
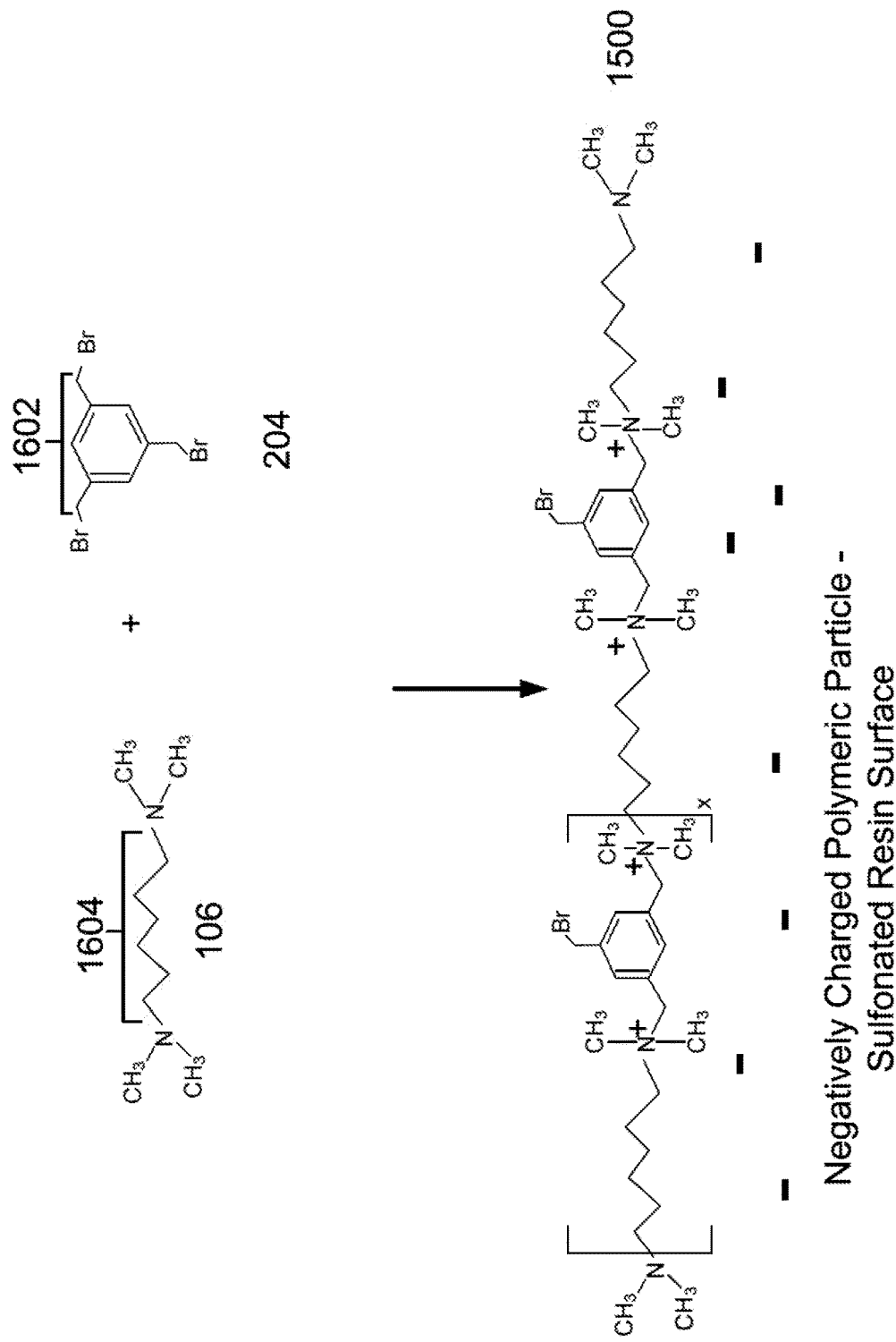
FIG. 15 illustrates a schematic representation of a base polymer layer formed from N,N,N',N'-tetramethyl-1,6-hexanediamine TMHDA and 1,3,5-tri(bromomethyl)benzene TBMB where the base polymer layer is attached to a negatively charged substrate particle.

In another embodiment, a hyperbranched ion exchange stationary phase will be described that uses a trihaloalkylaryl compound and a polyalkyldiamine. FIG. 15 illustrates a schematic representation of a base condensation polymer layer 1500 formed from a reaction with a first TMHDA 106 and a first TBMB 204 where the base polymer layer 1500 is attached to a negatively charged substrate particle. As illustrated in FIG. 15, the base condensation polymer layer 1500 includes quaternary amines. The term x in FIG. 15 may range from about 5 to about 150.

Base layer 1500 can be reacted with a number of reactions cycles of reagents to form a polyalkylpolyamine condensation polymer layer. In an embodiment, the number of reaction cycles may range from 1 to 10, preferably 3 to 10, and more preferably 3 to 6. Each reaction cycle includes a) a polyalkyldiiamine treatment and b) a trihaloalkylaryl treatment. After performing the number of reaction cycles, the polyalkylpolyamine condensation polymer layer may be reacted with a tertiary amine treatment to convert the remaining bromomethyl groups to quaternary amines.

Figure 16:
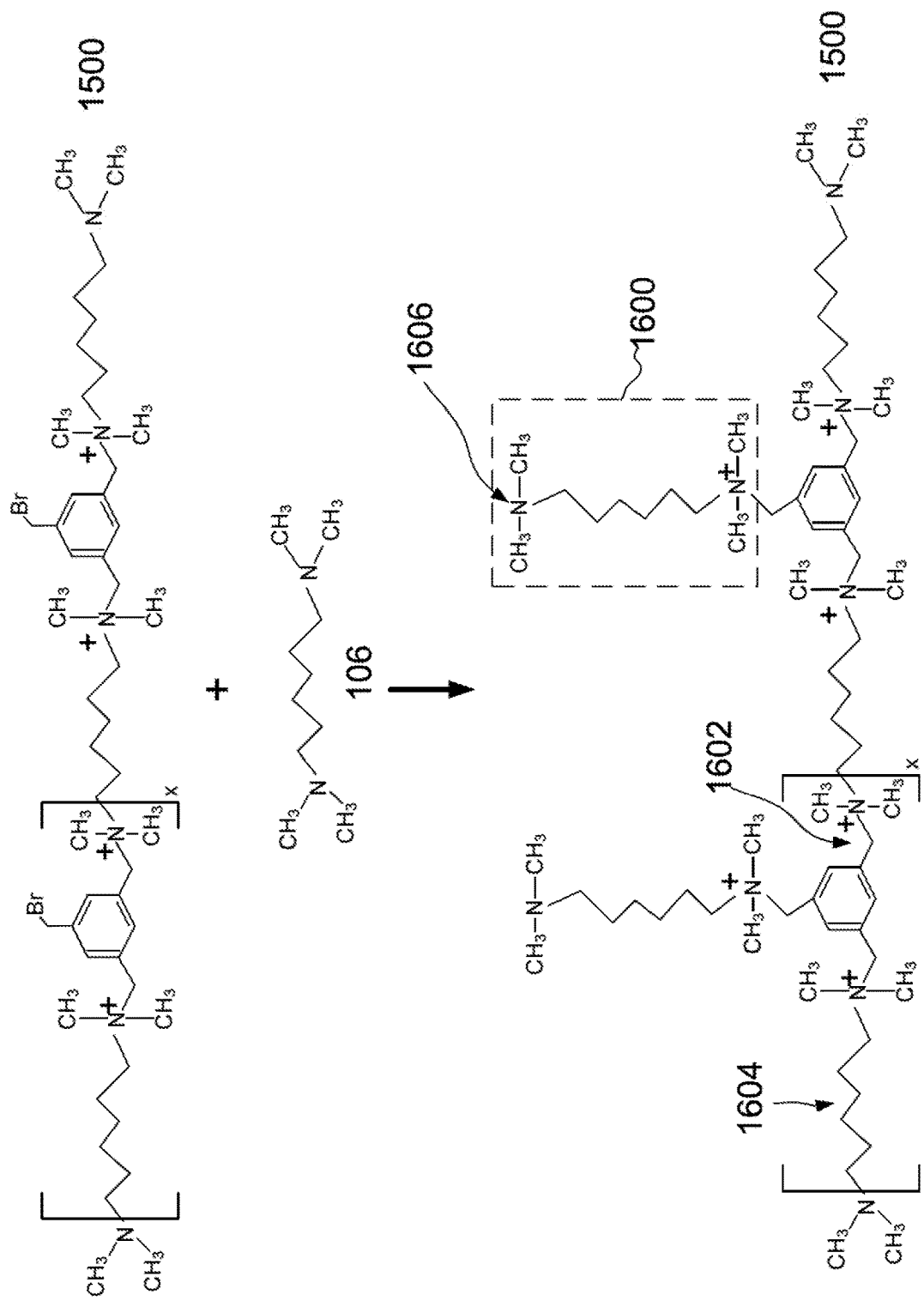
FIG. 16 illustrates a schematic of a first polyalkylpolyamine reaction product that has pendant tertiary amine groups and is covalently attached to the base polymer. The first polyalkylpolyamine reaction product is a reaction product of a halide group of the base polymer and a second TMHDA.

For the first step a) of a first cycle, a second TMHDA 106 can be reacted with pendant halide groups of base polymer layer 1500 to form a first polyalkylpolyamine CRP 1600, as illustrated in FIG. 16. The quaternary amines of the base condensation polymer layer 1500 are spaced apart by either a first spacer 1602 or a second spacer 1604. The first spacer 1602 is derived from TBMB 204 and the second spacer 1604 is derived from TMHDA 106, as shown in FIGS. 15 and 16.

Figure 17:
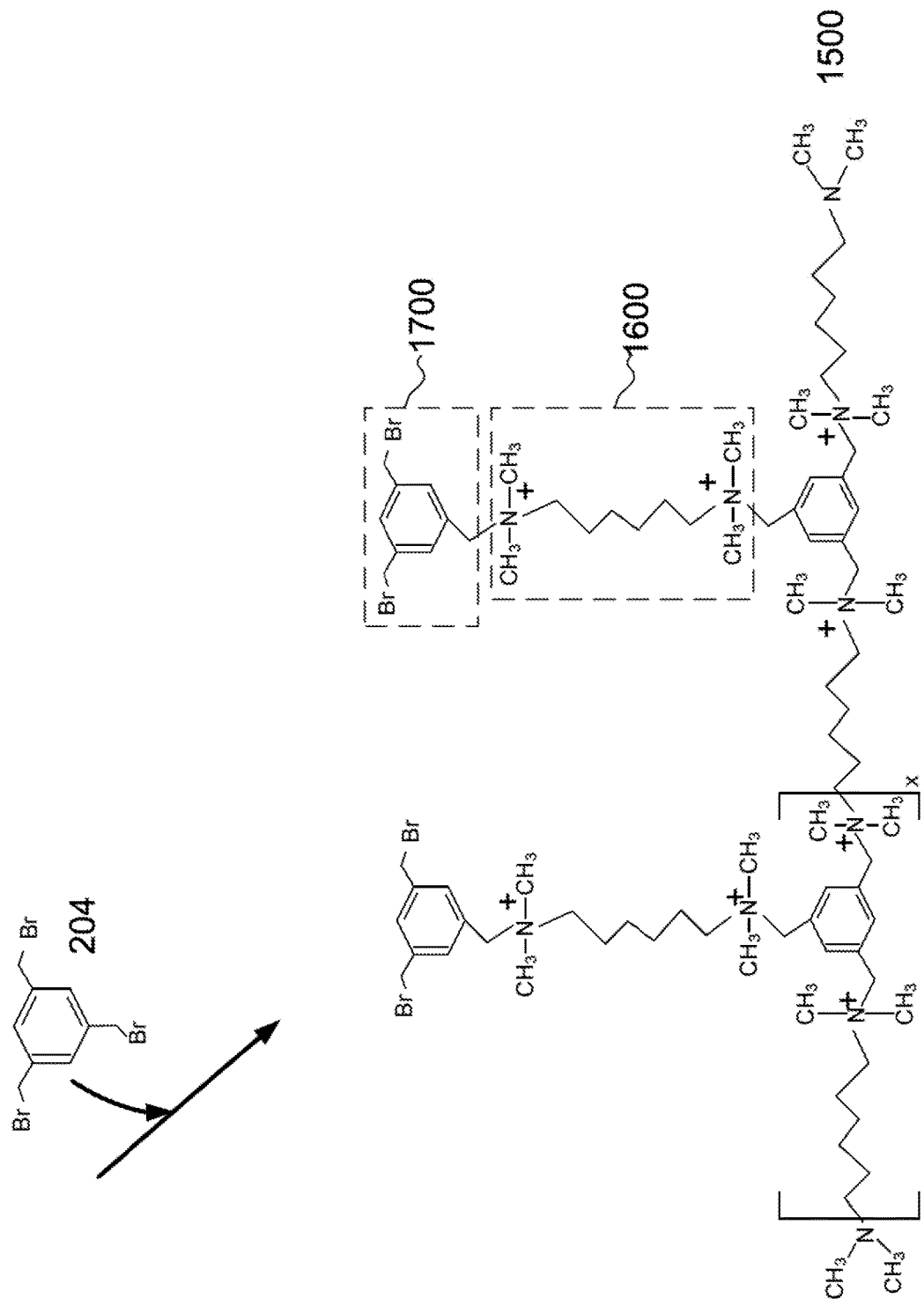
FIG. 17 illustrates a schematic of a first polyalkylaryl reaction product that is covalently attached to the first polyalkylpolyamine reaction product. The first polyalkylaryl reaction product is a reaction product of the pendant tertiary amine of the second TMHDA and a halide group of a second TBMB.

For a second step b) of the first cycle, a pendant tertiary amine 1606 of the first polyalkylpolyamine CRP 1600 can be reacted with a second TBMB 204 (a second trihaloalkylaryl) to form a first polyalkylaryl CRP 1700, as illustrated in FIG. 17. The first polyalkylaryl CRP 1700 is covalently attached to the first polyalkylpolyamine CRP 1600. The first polyalkylaryl CRP 1700 includes two halide groups per benzyl ring, as illustrated in FIG. 17.

Figure 18:
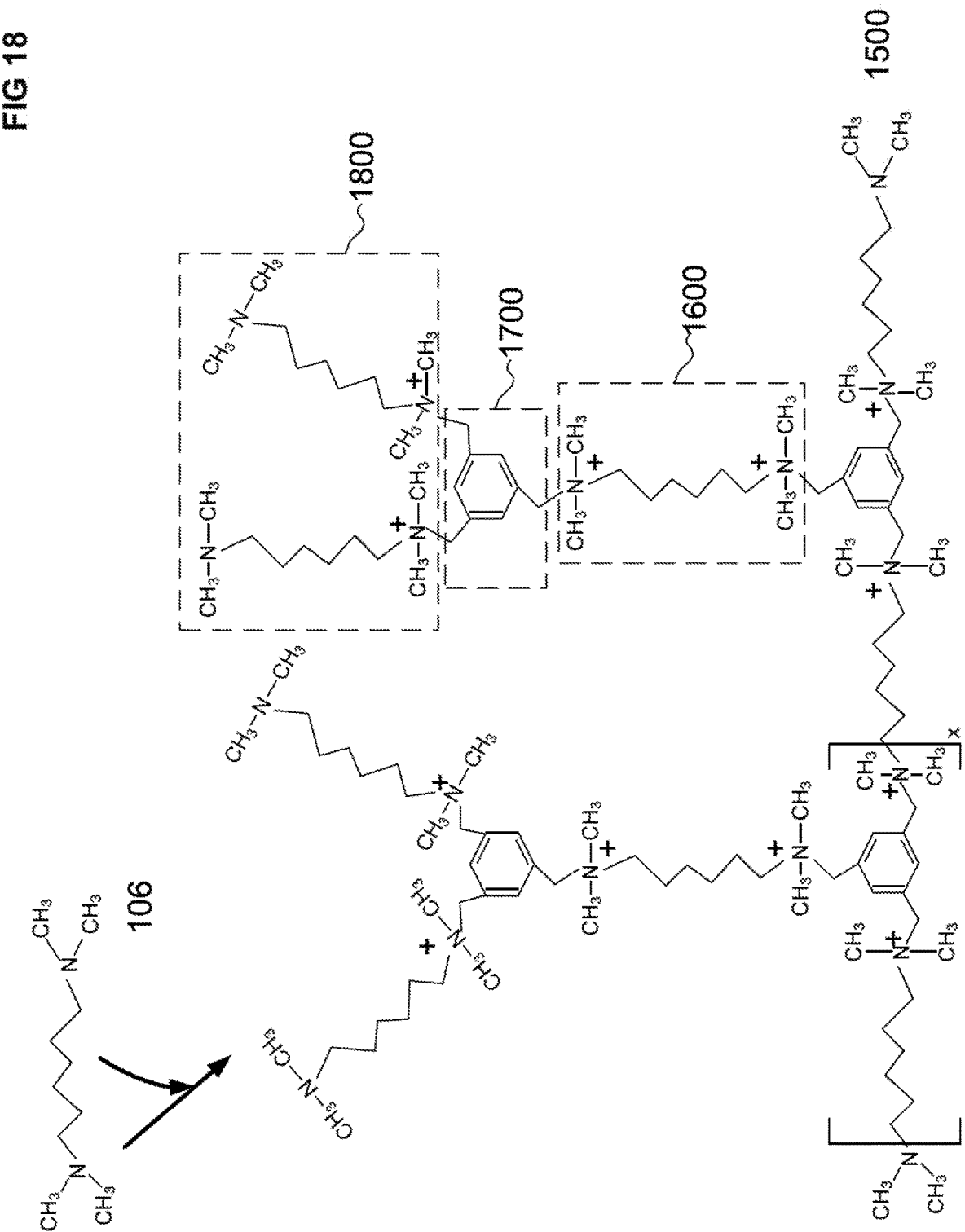
FIG. 18 illustrates a schematic of a second polyalkylpolyamine reaction product that has a pendant tertiary amine groups and is covalently attached to the first polyalkylaryl reaction product. The second polyalkylpolyamine reaction product is a reaction product of the halide groups of the first polyalkylaryl reaction product and a third TMHDA.

Now that one reaction cycle of two steps has been performed, a second cycle of two steps may be performed to create a hyperbranched structure. For a first step a) of a second cycle, two halide groups per benzyl ring of the polyalkylaryl CRP 1700 can be reacted with a third TMHDA 106 to form a second polyalkylpolyamine CRP 1800, as illustrated in FIG. 18. The second polyalkylpolyamine CRP 1800 is covalently attached to the first polyalkylaryl CRP 1700.

For a second step b) of the second cycle, the pendant tertiary amine groups of the second polyalkylpolyamine CRP 1800 can then be reacted with a third TBMB 204 to form a second polyalkylaryl CRP 1900, as illustrated in FIG. 19. The second polyalkylaryl CRP 1900 is covalently attached to the second polyalkylpolyamine CRP 1800.

A third reaction cycle of two steps can be performed with the second polyalkylaryl CRP 1900. For a first step a) of a third cycle, two halide groups per benzyl ring of the second polyalkylaryl CRP 1900 can be reacted with a fourth TMHDA 106 to form a third polyalkylpolyamine CRP (not shown). The third polyalkylpolyamine CRP is covalently attached to the second polyalkylaryl CRP 1900. It should be noted that the structure of the third polyalkylpolyamine CRP is analogous to the structure of the second polyalkylpolyamine CRP 1800.

For a second step b) of the third cycle, the pendant tertiary amine groups of the third polyalkylpolyamine CRP can then be reacted with a fourth TBMB 204 to form a third polyalkylaryl CRP (not shown). The third polyalkylaryl CRP is covalently attached to the third polyalkylpolyamine CRP (not shown). It should be noted that the structure of the third polyalkylaryl CRP is analogous to the structure of the second polyalkylaryl CRP 1900.

In an embodiment, more than 3 cycles may be performed by repeating steps a) and b). When the number of reaction cycles are completed, the polyalkylpolyamine condensation polymer layer may be reacted with a tertiary amine treatment to convert the remaining bromomethyl groups to quaternary amines. It should also be noted that FIGS. 15 to 19 are exemplary and that TMHDA may be substituted with other polyalkylpolyamines having at least two amine groups and that TBMB 204 may also be substituted with other polyhalogenhydrocarbons having three or more halide groups.

Figure 14:
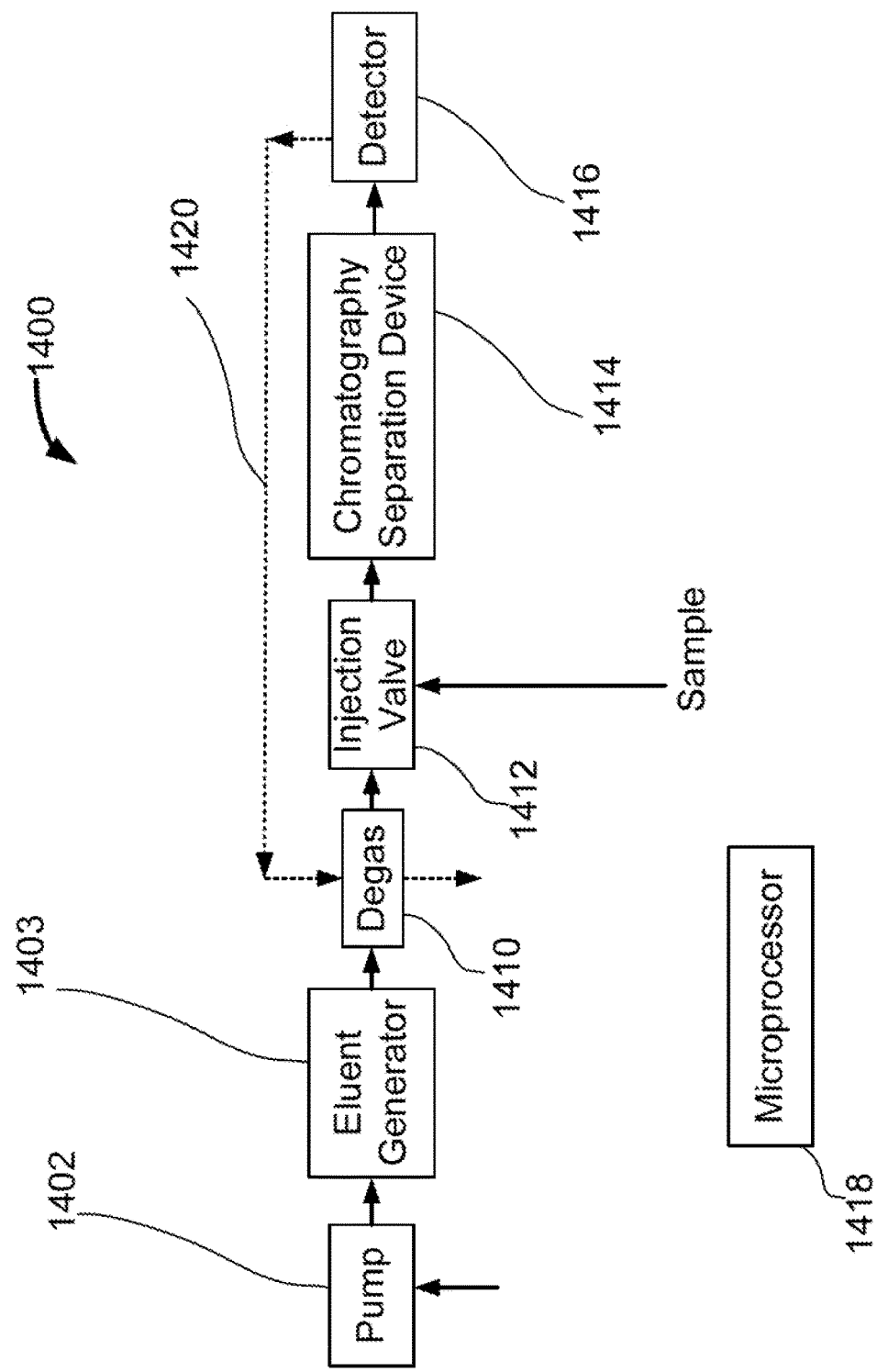
FIG. 14 shows an ion chromatography system suitable for analyzing samples with an ion exchange chromatography column and an electrochemical detector using quadruple voltage waveforms.

The following will describe chromatography systems suitable for use with the waveforms that includes a four voltage. FIG. 14 illustrates an embodiment of a chromatography system, which is an ion chromatography system 1400 that includes a pump 1402, an electrolytic eluent generating device 1403, a degas assembly 1410, an injection valve 1412, a chromatography separation device 1414, a detector 1416, and a microprocessor 1418. A recycle line 1420 may be used to transfer the liquid from an output of detector 1416 to a regenerant channel of degas assembly 1410. The degas assembly may also be in the form of a vacuum degasser.

Pump 1402 can be configured to pump a liquid from a liquid source and be fluidically connected to electrolytic eluent generating device 1403. Electrolytic eluent generating device 1403 is configured to generate an eluent such as for example NaOH or methanesulfonic acid. Details regarding electrolytic eluent generating devices (e.g., eluent generator) can be found in U.S. Pat. Nos. 6,225,129 and 6,682,701. In an embodiment, a residual gas such as carbon dioxide, hydrogen, and oxygen may be generated or be present in the eluent. This gas can be swept out with degas assembly 1410 using a recycled liquid via a recycle line 1420 that is downstream of detector 1416. Injection valve 1412 can be used to inject an aliquot of a sample into an eluent stream. Chromatography separation device 1414 (e.g., ion exchange chromatography column) can be used to separate various matrix components present in the liquid sample from the analytes of interest. An output of chromatography separation device 1414 can be fluidically connected to detector 1416 to measure the presence of the separated chemical constituents of the liquid sample. Chromatography separation device 1414 can separate one or more analytes of a sample that is outputted from chromatography separation device 1414 at different retention times.

Detector 1416 can be in the form of an electrochemical detector that includes a flow channel configured to be in fluidic contact with at least a working electrode, a reference electrode, and optionally a counter electrode. Details regarding an electrochemical detector flow cell and a disposable working electrode can be found in U.S. Pat. Nos. 8,925,374; 8,342,007; and 6,783,645, which are hereby fully incorporated by reference herein. The electrochemical detector also includes a potentiostat or an analytic device to apply a voltage waveform across the working electrode and reference electrode, and optionally passes a current between the counter electrode and working electrode. Details regarding an analytic device to apply a quadruple voltage waveform can be found in U.S. Pat. No. 8,636,885, which is hereby fully incorporated by reference herein.

An electronic circuit may include microprocessor 1418 and a memory portion. Microprocessor 1418 can be used to control the operation of chromatography system 1400. Microprocessor 1418 may either be integrated into chromatography system 1400 or be part of a personal computer that communicates with chromatography system 1400. Microprocessor 1418 may be configured to communicate with and control one or more components of chromatography system such as pump 1402, electrolytic eluent generating device 1403, injection valve 1412, and detector 1416. Memory portion can contain instructions on the magnitude, polarity, and timing for how to apply one or more voltage waveforms. In terms of measurement, memory portion can also contain instructions regarding which time periods to sample current values to integrate the signal and/or measuring a total charge for a particular time period.

EXAMPLE 1

Synthesis of the Anion Exchange Resin Using Pentamethyldipropyltriamine and 1,4-Diaminobutane A 4×250 mm (diameter×length) chromatography column was packed with 6.5 μm diameter particles with surface sulfonated (one hour at room temperature) 20.8 m²/g wide-pore (DVB/EVB). The base condensation layer was applied to a packed column by flowing a pentamethyldipropyltriamine (PMDPTA): 1,4-diaminobutane (DBB) solution mixture (1:1 mole ratio in 20% methanol/80% acetonitrile, 50% (wt/wt %) with respect to PMDPTA: 38% (wt/wt %) with respect to DBB) at 0.5 mL/minute through the column at 70° C. for 90 minutes to form a base condensation polymer 300 (see FIG. 3). Next, 4 cycles of reagent treatment were flowed at 0.5 mL/minute through the column at 70° C. A single cycle of reagent treatment included a first step a) 38% (wt/wt %) DBB solution in 20% methanol/80% acetonitrile was flowed through the column for 60 minutes to form a first alkyl condensation reaction product 400 (see FIG. 4), and a second step b) 50% (wt/wt %) PMDPTA solution in 20% methanol/80% acetonitrile was flowed through the column for 60 minutes to form a first polyalkylpolyamine condensation reaction product 500 (see FIG. 5). After completing the first cycle of reagent treatment (steps a) to b)), three additional cycles of reagent treatment were performed.

EXAMPLE 2

Synthesis of Pentamethyldihexyltriamine (PMDHTA)

Formic acid (150 mL) was added dropwise to a mixture of bis(hexamethylene)triamine (86 grams) and formaldehyde solution (37%, 223 mL) at 65° C. during a one hour time period. The reaction was allowed to continue for an additional three hours. After cooling the reaction to ambient temperature, sodium hydroxide (solid, flake, purity: 97%) was added until the pH was 14. The reaction mixture was extracted with diethyl ether, washed with brine (saturated NaCl solution), and then dried with magnesium sulfate. After the volatiles were removed with a rotary evaporator, the residue was purified by Kugelrohr distillation at 1.2 mm Hg and 140° C. to yield 63 grams of PMDHTA.

EXAMPLE 3

Synthesis of the Anion Exchange Resin Using Pentamethyldihexyltriamine and 1,4-Diaminobutane 6.2 grams of super macroporous resin particles were used that have a surface sulfonation (one hour at room temperature), 6.5 μm diameter, and 20.8 m²/g wide-pore (DVB/EVB). The resin was rinsed with isopropyl alcohol (IPA) to remove water. The rinsed resin was transferred to a vial. Next, the following ingredients were added to the vial, which were 6.0 grams of IPA, 2.9 grams PMDHTA, and 2 grams DBB. The vial with added ingredients was heated to 70° C. and allowed to react for 165 minutes. The reacted ingredients from the vial formed the base condensation layer attached to the resin particles, which were filtered and then washed with IPA.

Next, the filtered particles with the base condensation layer were added to a vial where three cycles of reagent treatment were performed at 70° C. A single cycle of reagent treatment included a first reaction step a) 6 grams of IPA and 2 grams DBB were added to the vial containing the filtered particles and allowed to react for 120 minutes at 70° C. After the reaction, the contents of the vial were filtered and washed with IPA. The second reaction step b) 2 grams of IPA and 1.5 grams PMDHTA were added to the vial containing the filtered particles of step a) and allowed to react for 120 minutes at 70° C. After the reaction, the contents of the vial were filtered and washed with IPA. After completing the first cycle of reagent treatment (steps a) to b)), two additional cycles of reagent treatment were performed that resulted in a polyalkylpolyamine layer being bound to the base condensation layer.

Next, the filtered particles with the polyalkylpolyamine layer were added to a vial so that any remaining tertiary amines can be quaternized. 2 grams of IPA and 1.5 grams methyliodide was added to the vial containing the filtered particles and allowed to react for 120 minutes at 70° C. After the reaction, the contents of the vial were filtered and washed with IPA, water, and 1 M NaOH. The filtered and washed particles were packed into a chromatography column.

EXAMPLE 4

Synthesis of the Anion Exchange Resin Using N,N,N',N'-Tetramethyl-1,6-hexanediamine and 1,3,5-Tri(bromomethyl)benzene 6.4 grams of super macroporous resin particles were used that have a surface sulfonation (one hour at room temperature), 6.5 μm diameter, and 20.8 m²/g wide-pore (DVB/EVB). The resin was rinsed with a solvent mixture (20% methanol/80% acetonitrile) to remove water. The rinsed resin was transferred to a vial. Next, 6.0 grams of the solvent mixture and 1.35 grams of 1,3,5-tri(bromomethyl)benzene (TBMB) were added to the vial and heated in a capped vial at 50° C. in an oven for 10 minutes to dissolve the TBMB. 0.65 grams of N,N,N',N'-tetramethyl-1,6-hexanediamine (TMHDA) was dissolved in another vial using 1.5 grams of the solvent mixture. The dissolved TMHDA was added dropwise to the vial containing TBMB while stirring. The vial was then capped and allowed to react at 50° C. for 30 minutes. After the reaction, the contents of the vial were filtered and washed with solvent mixture to yield resin particles with a base condensation layer.

Next, the filtered particles with the base condensation layer were added to a vial where three cycles of reagent treatment were performed at 50° C. A single cycle of reagent treatment included a first reaction step a) 3 grams of the solvent mixture (20% methanol/80% acetonitrile) and 0.9 grams TMHDA were added to the vial containing the filtered particles and allowed to react for 30 minutes at 50° C. After the reaction, the contents of the vial were filtered and washed with the solvent mixture. The second reaction step b) 3 grams of the solvent mixture and 0.9 grams TBMB were added to the vial containing the filtered particles of step a) and allowed to react for 30 minutes at 50° C. After the reaction, the contents of the vial were filtered and washed with the solvent mixture. After completing the first cycle of reagent treatment (steps a) to b)), two additional cycles of reagent treatment were performed that resulted in a polyalkylpolyamine layer bound to the base condensation layer.

Next, the filtered particles with the polyalkylpolyamine layer were added to a vial so that any remaining bromomethyl groups can be reacted. 2 grams of the solvent mixture and 1.5 grams of 33% trimethylamine in ethanol was added to the vial containing the filtered particles and allowed to react overnight at ambient temperature. After the reaction, the contents of the vial were filtered and washed with the solvent mixture, water, and 1 M NaOH. The filtered and washed particles were packed into a chromatography column.

EXAMPLE 5

Chromatograms of a Standard Solution Containing Various Carbohydrates Using a Range of Eluent Concentrations with Anion Exchange Resin Based on PMDHTA and DBB The chromatography column of Examples 3 was installed into a Thermo Scientific Dionex ICS-5000⁺ ion chromatography system (commercially available from Thermo Fisher Scientific, Sunnyvale, Calif.) with a format similar to FIG. 14. A pump was used to pump deionized water into a Thermo Scientific Dionex EGC 500 NaOH cartridge (Thermo Fisher Scientific, Sunnyvale, California) for generating a NaOH at one of six different concentrations that were 10, 20, 30, 40, 50, and 60 mM NaOH. A temperature regulator was used to maintain a column temperature of 30° C. The flow rate was 1 mL/min and the injection volume was 25 μL. The detector was a Thermo Scientific electrochemical detector fitted with disposable PTFE gold electrodes. The detector was operated in the integrated pulsed amperometric mode using a quadruple waveform. Table 1 shows the applied potentials and time durations of the quadruple voltage waveform.

TABLE 1

| Time (s) | Potential (V) | Integration |
|---|---|---|
| 0.00 | 0.10 | |
| 0.20 | 0.10 | Start |
| 0.40 | 0.10 | End |
| 0.41 | −2.00 | |
| 0.42 | −2.00 | |
| 0.43 | 0.60 | |
| 0.44 | −0.10 | |
| 0.50 | −0.10 | |

Figure 8:
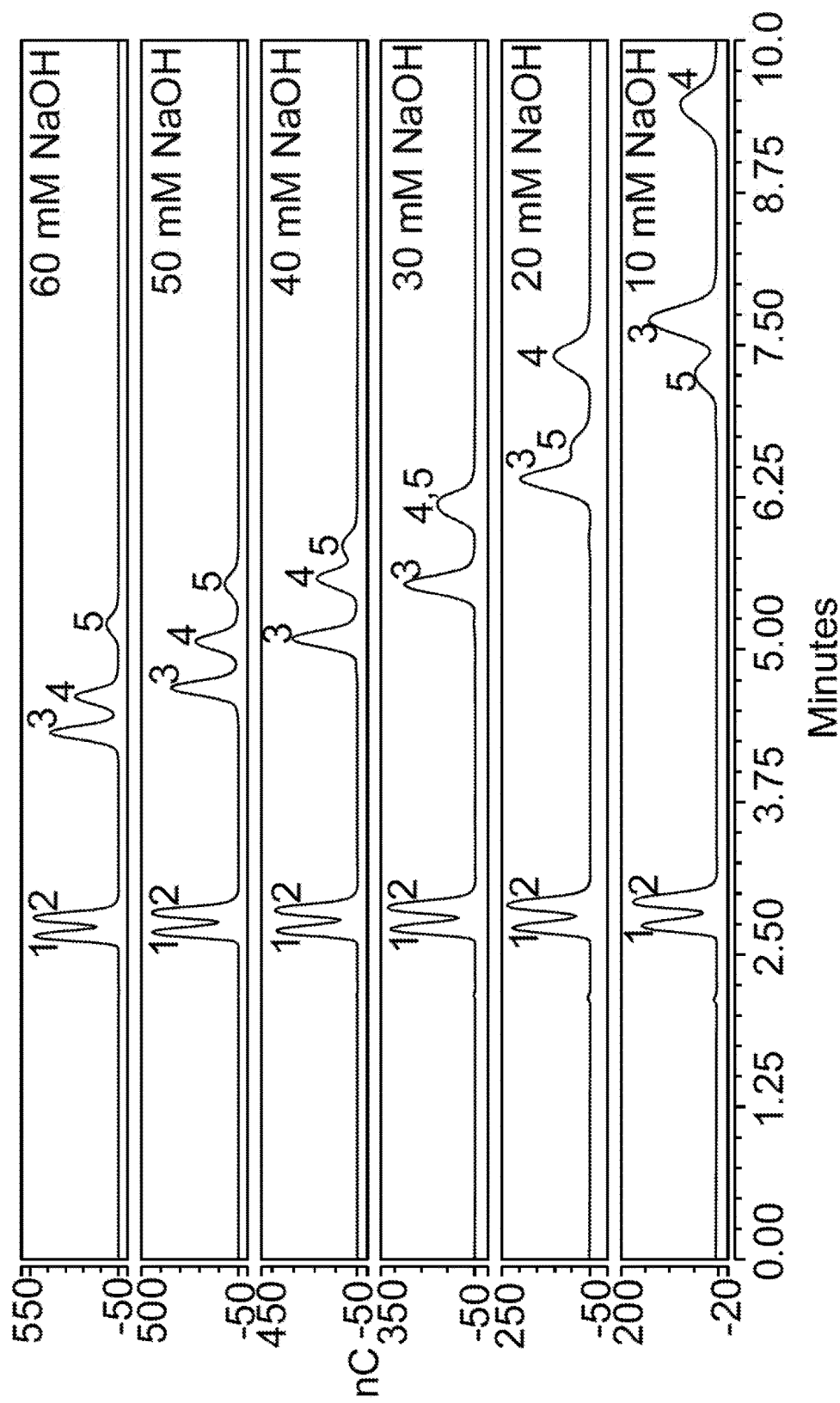
FIG. 8 illustrates six chromatograms where each one uses a different NaOH eluent concentration and a standard solution containing five different carbohydrates. The chromatograms were performed using an anion exchange resin that includes pentamethyldihexyltriamine PMDHTA and 1-4-dibromobutane DBB.

FIG. 8 illustrates six chromatograms where each one uses a different NaOH eluent concentration. The chromatograms were performed using an anion exchange resins that include PMDHTA and DBB and a standard solution containing five different carbohydrates, which were dulcitol (peak 1 at 10 ppm), mannitol (peak 2 at 10 ppm), glucose (peak 3 at 10 ppm), fructose (peak 4 at 10 ppm), sucrose (peak 5 at 10 ppm), and lactose (peak 6 at 10 ppm). The dulcitol and mannitol (peaks 1 and 2, respectively) had relatively constant retention times over the tested range of NaOH concentration. In contrast, the glucose, fructose, and sucrose peaks (peaks 3, 4, and 5, respectively) had increasing retention time with decreasing NaOH eluent concentration. The increase of retention time for peaks 3-5 each had a different dependence on eluent concentration so that the peak elution order was different for 60 mM NaOH and 10 mM NaOH. This change in order of the peaks 3-5 provides an advantage of more flexibility in manipulating the retention time of the peaks that may be needed to avoid potentially interfering anions that can be present. The fact that sucrose (pKa of 12.62) elutes well before fructose (pKa of 12.03) with a 10 mM NaOH eluent (pH 12) indicates that the stationary phase pH is less than the pH of the latex-based Thermo Scientific Dionex CarboPac PA1 stationary phase. When using CarboPac PA1 stationary phase, Applicant found that fructose and sucrose co-elute under the same conditions. Such differences in stationary phase pH are useful in providing alternative separation selectivity in cases where existing commercial columns cannot separate important mixtures of carbohydrates at low eluent concentrations (e.g., 10 mM).

EXAMPLE 6

Chromatograms of Standard Solutions Containing Various Carbohydrates Using the Anion Exchange Resin Based on PMDHTA and DBB The chromatography column of Example 3 was installed into a Thermo Scientific Dionex ICS-5000⁺ ion chromatography system (commercially available from Thermo Fisher Scientific, Sunnyvale, California) with a format and conditions that were similar as Example 5. However, the eluent concentration was held constant at 60 mM NaOH and an additional standard solution that contained sucrose and lactose was used.

Figure 9:
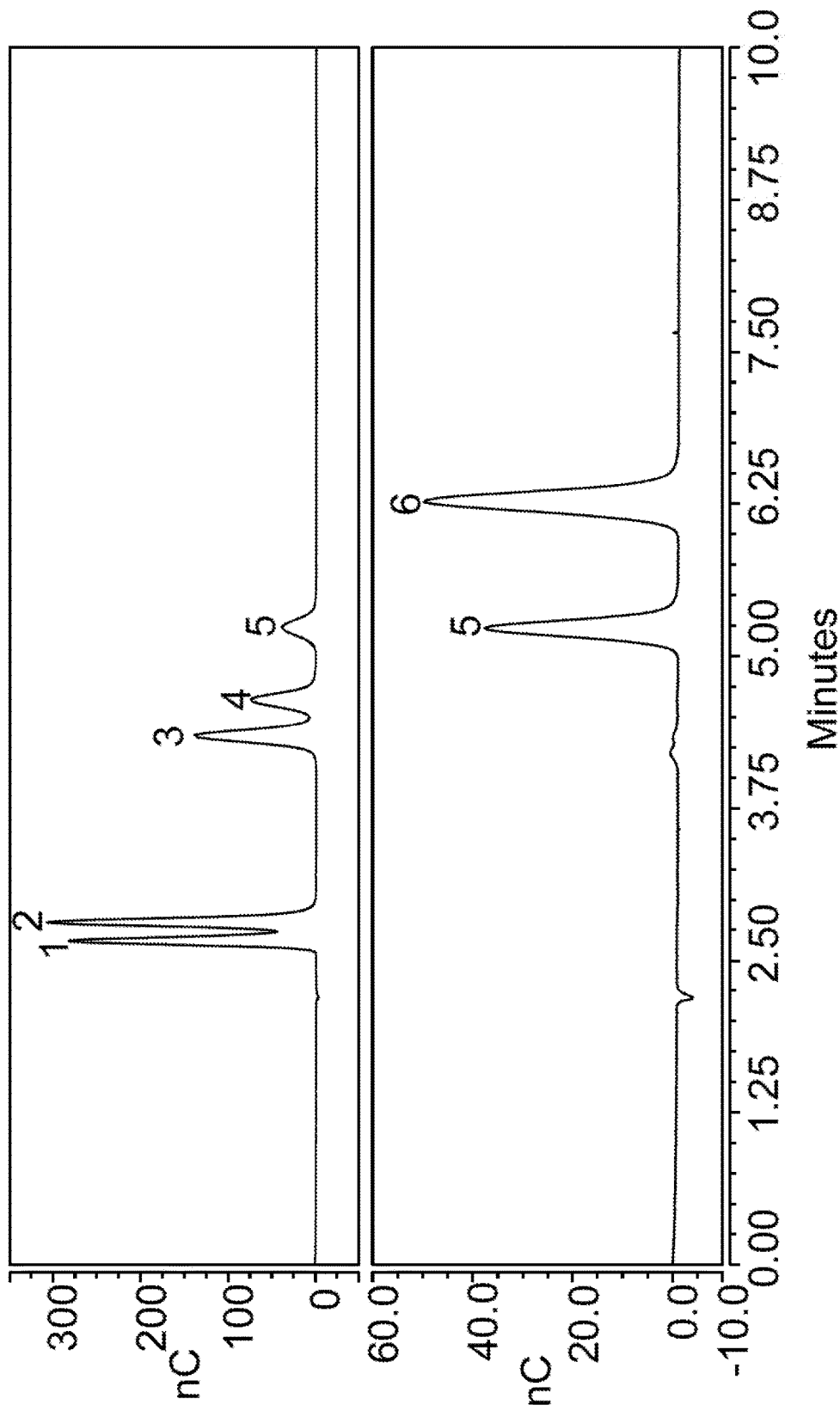
FIG. 9 illustrates two chromatograms using the anion exchange resin that includes PMDHTA and DBB. A standard solution was injected into a chromatography column that contained either five carbohydrates (upper chromatogram) or two carbohydrates (lower chromatogram).

FIG. 9 illustrates two chromatograms where the upper chromatogram used the standard solution of Example 5 and the lower chromatogram used a standard solution containing sucrose and lactose (peaks 5 at 10 ppm and peak 6 at 10 ppm, respectively). The chromatograms were performed using a chromatography column containing the same anion exchange resin of Example 5. The upper and lower chromatograms together suggest that all six carbohydrates can be resolved in one chromatography run. In the lower chromatogram, it should be noted that sucrose and lactose (peaks 5 and 6, respectively) were fully resolved, which is an advantage in that these carbohydrates are difficult to resolve under the chromatographic conditions.

EXAMPLE 7

Chromatograms of a Standard Solution Containing Various Carbohydrates Using a Range of Eluent Concentrations with Anion Exchange Resin Based on TBMB and TMHDA The chromatography column of Examples 4 was installed into a Thermo Scientific Dionex ICS-5000+ ion chromatography system (commercially available from Thermo Fisher Scientific, Sunnyvale, Calif.) with a format similar to Example 5. In contrast to Example 5, only three NaOH concentrations were used instead of six. The three NaOH concentrations were 10, 30, and 60 mM NaOH.

Figure 10:
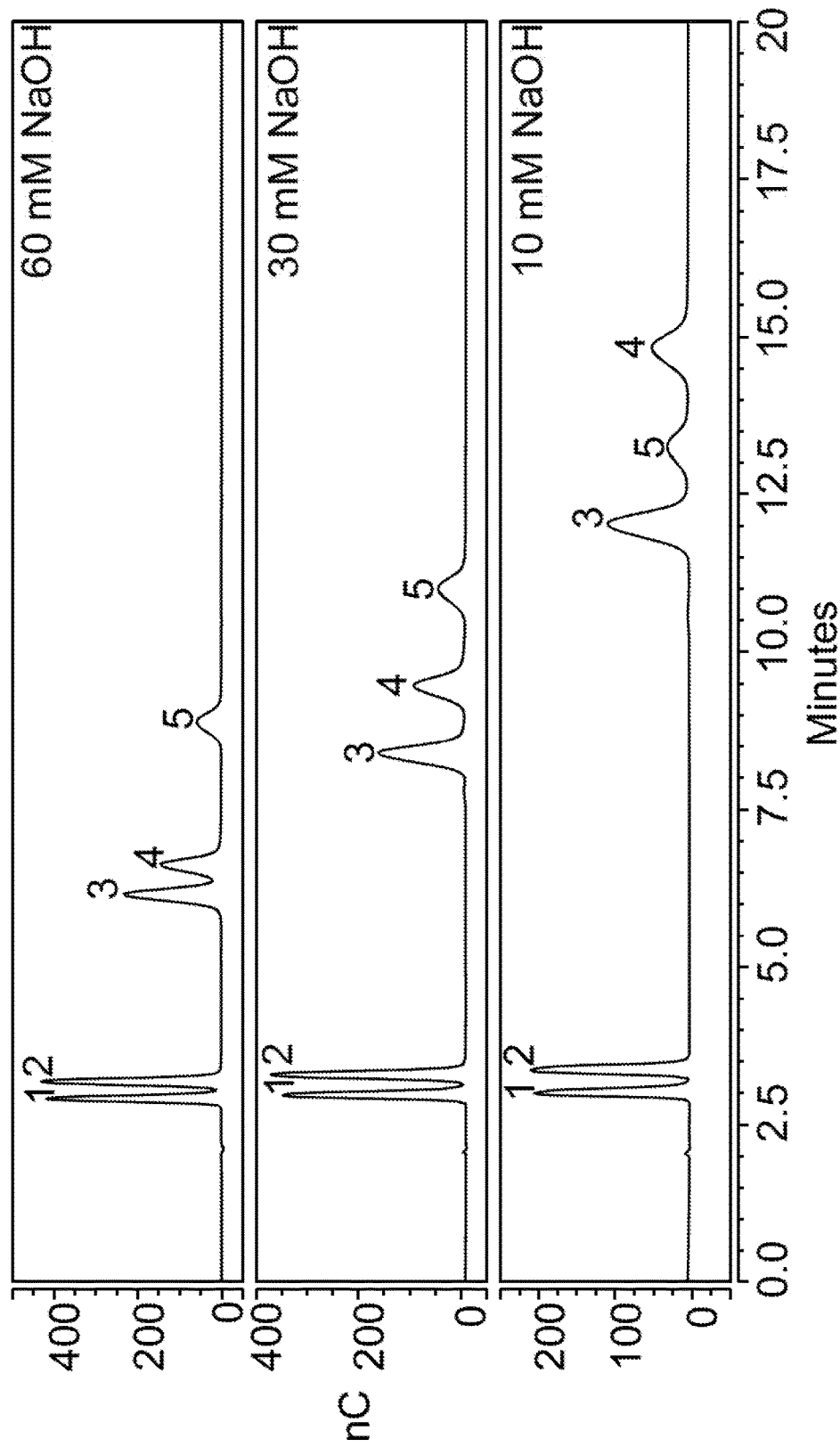
FIG. 10 illustrates three chromatograms where each one uses a different NaOH eluent concentration and a standard solution containing five different carbohydrates. The chromatograms were performed using an anion exchange resin that includes N,N,N',N'-tetramethyl-1,6-hexanediamine TMHDA and 1,3,5-tri(bromomethyl)benzene TBMB.

FIG. 10 illustrates three chromatograms where each one uses a different NaOH eluent concentration. The chromatograms were performed using an anion exchange resins that include TBMB and TMHDA and a standard solution containing five different carbohydrates, which were dulcitol (peak 1 at 10 ppm), mannitol (peak 2 at 10 ppm), glucose (peak 3 at 10 ppm), fructose (peak 4 at 10 ppm), sucrose (peak 5 at 10 ppm), and lactose (peak 6 at 10 ppm). Similar to Example 5, the dulcitol and mannitol (peaks 1 and 2, respectively) had relatively constant retention times over the tested range of NaOH concentration. Similar to Example 5, the glucose, fructose, and sucrose peaks (peaks 3, 4, and 5, respectively) had increasing retention time with decreasing NaOH eluent concentration. The increase of retention time for peaks 3-5 each had a different dependence on eluent concentration so that the peak elution order was different for 60 mM NaOH and 10 mM NaOH. This change in order of the peaks 3-5 provides an advantage of more flexibility in manipulating the retention time of the peaks that may be needed to avoid potentially interfering anions that can be present.

EXAMPLE 8

Chromatograms of Standard Solutions Containing Various Carbohydrates Using the Anion Exchange Resin Based on TBMB and TMHDA The chromatography column of Example 4 was installed into a Thermo Scientific Dionex ICS-5000+ ion chromatography system (commercially available from Thermo Fisher Scientific, Sunnyvale, California) with a format and conditions that were similar as Example 6.

Figure 11:
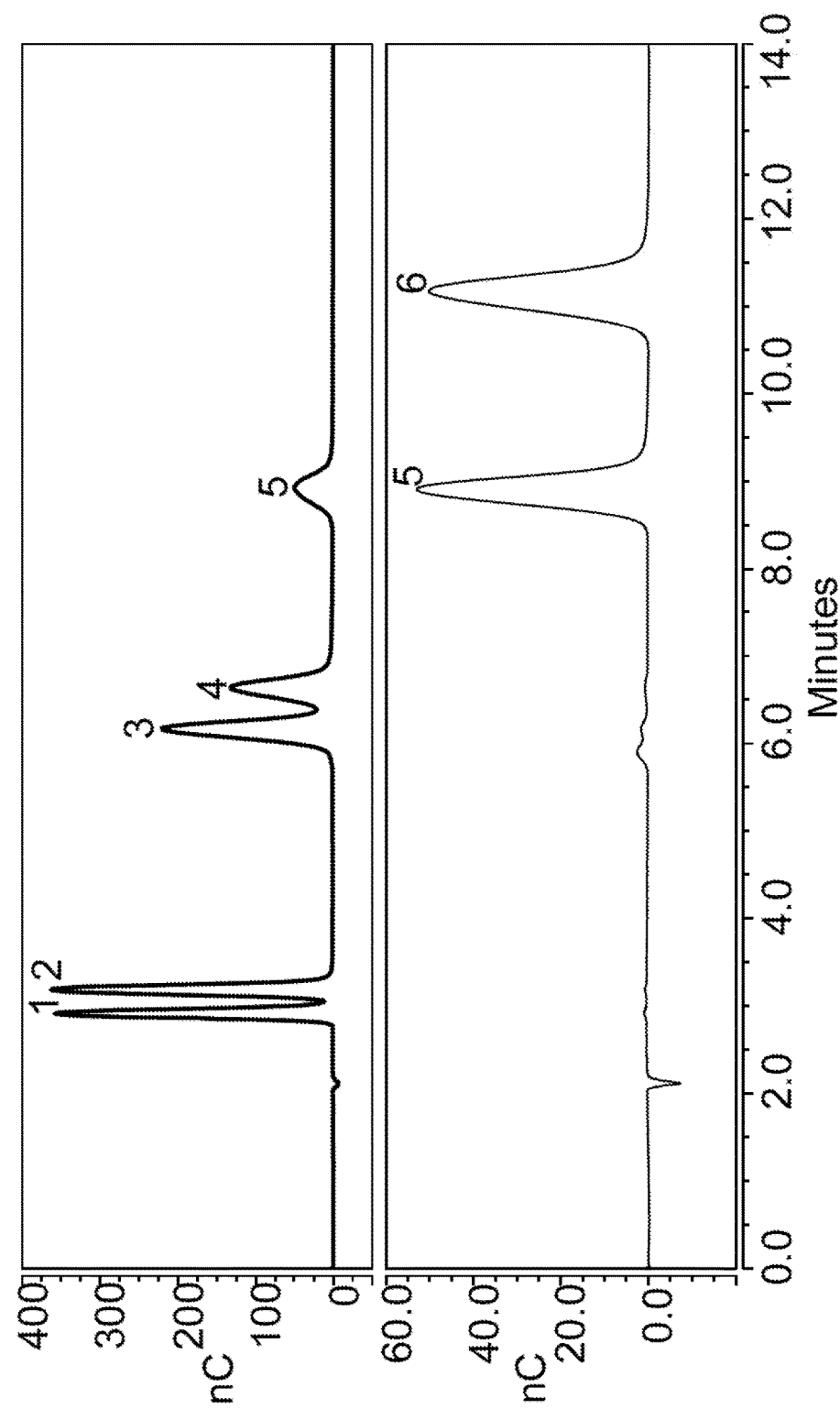
FIG. 11 illustrates two chromatograms using an anion exchange resin that includes TMHDA and TBMB. A standard solution was injected into a chromatography column that contained either five carbohydrates (upper chromatogram) or two carbohydrates (lower chromatogram).

FIG. 11 illustrates two chromatograms where the upper chromatogram used the standard solution of Example 5 and the lower chromatogram used a standard solution containing sucrose and lactose (peaks 5 at 10 ppm and peak 6 at 10 ppm, respectively). The chromatograms were performed using a chromatography column containing the same anion exchange resin of Example 4. The upper and lower chromatograms together suggest that all six carbohydrates can be resolved in one chromatography run. In the lower chromatogram, it should be noted that sucrose and lactose (peaks 5 and 6, respectively) were fully resolved, which is an advantage in that these carbohydrates are difficult to resolve under the chromatographic conditions.

EXAMPLE 9

Chromatograms of Sample Solutions Containing Fetuin Alditols Using Anion Exchange Resin Based on PMDHTA and DBB The chromatography column of Example 4 was installed into a Thermo Scientific Dionex ICS-5000+ ion chromatography system (commercially available from Thermo Fisher Scientific, Sunnyvale, California) with a format and conditions that were similar as Example 5. A pump was used to pump a mixture of three solutions (A. deionized water, B. 0.1 M NaOH, and C. 0.1 M NaOH and 0.25 M sodium acetate) with a gradient elution of 20 to 225 mM sodium acetate at 0.1 M NaOH in 80 minutes. A temperature regulator was used to maintain a column temperature of 30° C. The flow rate was 1 mL/min and the injection volume was 10 μL of 50 μM fetuin alditols. The alditols from fetuin were released using the enzyme PNGase F. The detector was a Thermo Scientific electrochemical detector fitted with disposable PTFE gold electrodes. The detector was operated in the integrated pulsed amperometric mode using a quadruple waveform as described in Table 1 of Example 5.

Figure 12:
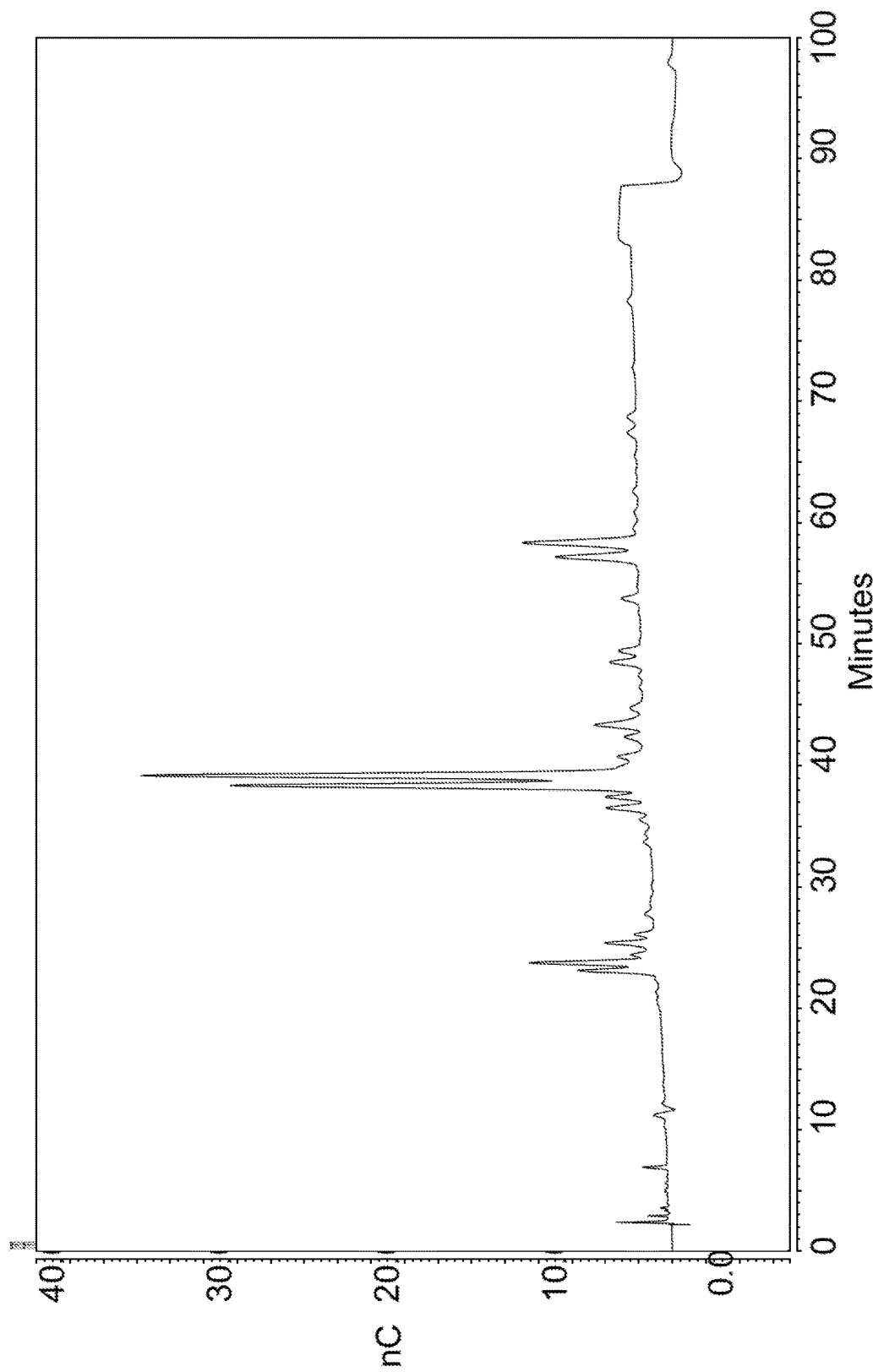
FIG. 12 illustrates a chromatogram using an anion exchange resin that includes PMDHTA and DBB that shows 38 peaks. A sample solution was injected into a chromatography column that contained fetuin alditols.

FIG. 12 illustrates a chromatogram using the anion exchange resin that includes PMDHTA and DBB. A sample solution was injected into a chromatography column that contained fetuin alditols that resulted in the measurement of 38 peaks. The chromatogram of FIG. 12 showed the utility of using the chromatography column of Example 4 to characterize glycans released from fetuin.

EXAMPLE 10

Figure 13:
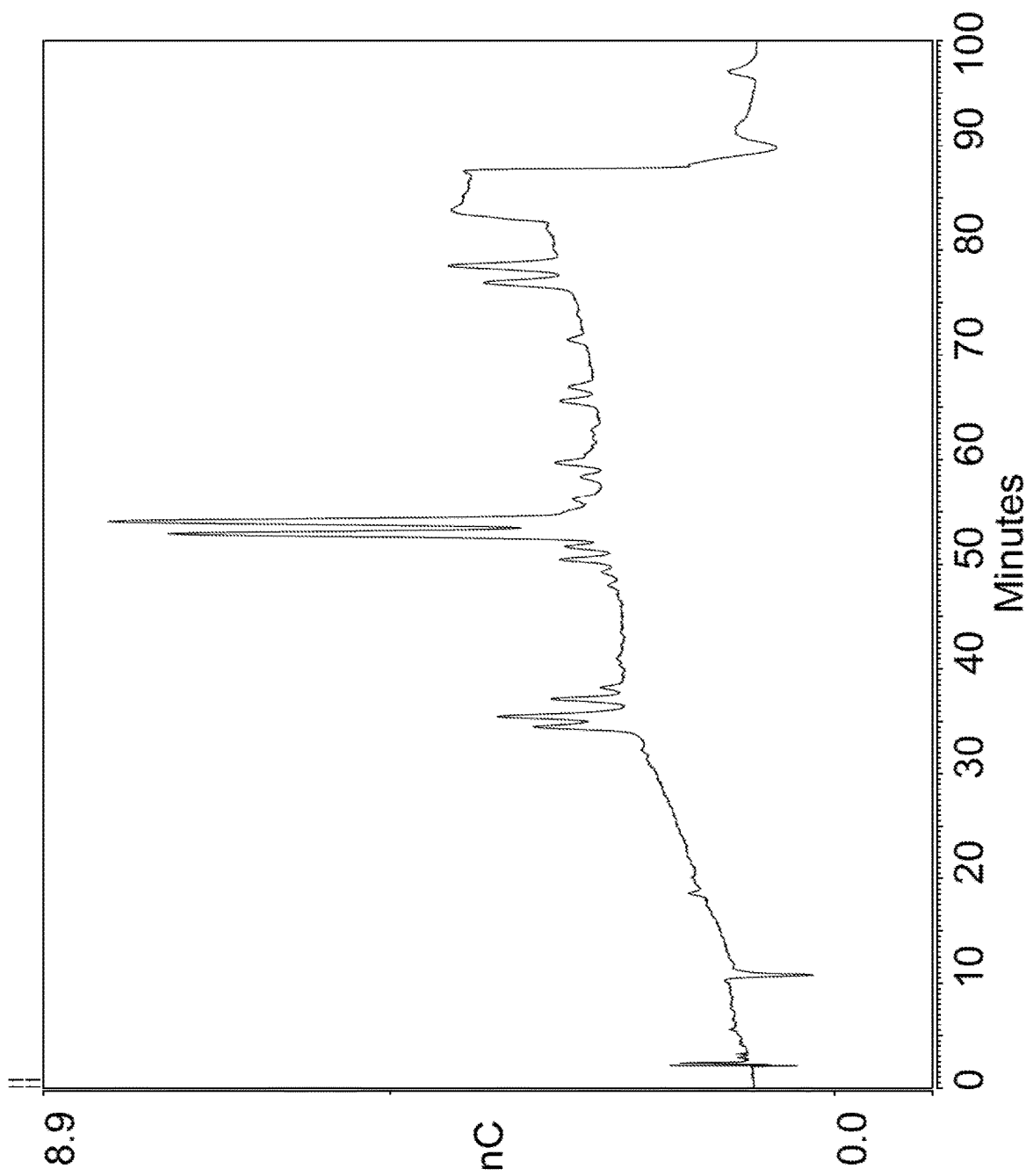
FIG. 13 illustrates a chromatogram using an anion exchange resins that include TMHDA and TBMB that shows 28 peaks. A sample solution was injected into a chromatography column that contained fetuin alditols.

Chromatograms of Sample Solutions Containing Fetuin Alditols Using Anion Exchange Resin Based on TBMB and TMHDA The chromatography column of Example 5 was installed into a Thermo Scientific Dionex ICS-5000+ ion chromatography system (commercially available from Thermo Fisher Scientific, Sunnyvale, California) with a format and conditions that were similar as Example 9. FIG. 13 illustrates a chromatogram using the anion exchange resin that includes TBMB and TMHDA. A sample solution was injected into a chromatography column that contained fetuin alditols that resulted in the measurement of 28 peaks. The chromatogram of FIG. 13 showed the utility of using the chromatography column of Example 5 to characterize glycans released from fetuin.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of using a chromatography column for separating a plurality of carbohydrates in a sample, the method comprising:
   flowing an eluent through the chromatography column, in which the eluent includes a hydroxide; injecting the sample comprising a plurality of carbohydrates into the chromatography column; separating at least one of the plurality of carbohydrates in the chromatography column; and detecting the at least one of the plurality of carbohydrates at a detector, wherein the
   chromatography column contains the anion exchange stationary phase, the phase formed by a method comprising:
      reacting a polyhalohydrocarbon with a polyalkylpolyamine to form a base condensation polymer layer on a negatively charged substrate particle; and
      reacting the base condensation polymer layer with a number of reaction cycles to form a polyalkylpolyamine condensation polymer layer, in which the number of reaction cycles ranges from about three to about ten and each reaction cycle includes a polyhalohydrocarbon treatment and a polyalkylpolyamine treatment, the polyalkylpolyamine condensation polymer layer formed from a polymerization reaction with a polyalkylpolyamine and a polyhalohydrocarbon, wherein all of the amine groups of the polyalkylpolyamine are tertiary amines, the polyalkylpolyamine condensation polymer layer comprising a polymeric branch structure, the polymeric branch structure comprises a hyperbranched polymer which has a structure that has an increasing number of branches as the polymer extends outwardly from the negatively charged substrate particle thereby having a density of a plurality of quaternary amines which increases in a direction away from the base condensation polymer layer;
      wherein the polyhalohydrocarbon is dibromobutane or tribromomethylbenzene, and the polyalkylpolyamine is pentamethylhexyltriamine or tetramethylhexanediamine.

2. The method of claim 1, wherein the reacting the polyhalohydrocarbon with the polyalkylpolyamine is performed in a solvent mixture, the solvent mixture having about four parts acetonitrile to about 1 part methanol.

3. The method of claim 1, wherein the at least one of the plurality of carbohydrates is a branched glycan.

4. The method of claim 1, wherein the plurality of carbohydrates comprises a fructose and a sucrose, wherein the separating of the at least one of the plurality of carbohydrates comprises separating the fructose and the sucrose in the chromatography column.

5. The method of claim 1, wherein the plurality of carbohydrates comprises a sucrose and a lactose, wherein the separating of the at least one of the plurality of carbohydrates comprises separating the sucrose and the lactose in the chromatography column.

6. A method of using a chromatography column for separating a plurality of carbohydrates in a sample, the method comprising:
   flowing an eluent through the chromatography column, in which the eluent includes a hydroxide; injecting the sample comprising a plurality of carbohydrates into the chromatography column; separating at least one of the plurality of carbohydrates in the chromatography column; and detecting the at least one of the plurality of carbohydrates at a detector, wherein the
   chromatography column contains the anion exchange stationary phase, the phase comprising:
      a) a negatively charged substrate particle;
      b) a base condensation polymer layer attached to the negatively charged substrate particle, the base condensation polymer layer comprising a first plurality of quaternary amines, in which the first plurality of quaternary amines are spaced apart by either a first spacer or a second spacer, in which the base condensation polymer layer does not have a hydroxy group spaced apart from one of the first plurality of quaternary amines by an ethyl group;
      c) a polyalkylpolyamine condensation polymer layer covalently attached to the base condensation polymer layer, the polyalkylpolyamine condensation polymer layer formed from a
      polymerization reaction with a polyalkylpolyamine and a polyhalohydrocarbon, wherein all of the amine groups of the polyalkylpolyamine are tertiary amines, the polyalkylpolyamine condensation polymer layer comprising a polymeric branch structure, the polymeric branch structure includes a second plurality of quaternary amines, in which the second plurality of quaternary amines are spaced apart by the first spacer or the second spacer, the polymeric branch structure comprises a hyperbranched polymer which has a structure that has an increasing number of branches as the polymer extends outwardly from the negatively charged substrate particle thereby having in which a density of the second plurality of quaternary amines which increases in a direction away from the base condensation polymer layer, in which the polyalkylpolyamine condensation polymer layer does not have a hydroxy group spaced apart from one of the second plurality of quaternary amines by an ethyl group;
      wherein the polyhalohydrocarbon is dibromobutane or tribromomethylbenzene, and the polyalkylpolyamine is pentamethylhexyltriamine or tetramethylhexanediamine.

7. The method of claim 6, wherein the at least one of the plurality of carbohydrates is a branched glycan.

8. The method of claim 6, wherein the plurality of carbohydrates comprises a fructose and a sucrose, wherein the separating of the at least one of the plurality of carbohydrates comprises separating the fructose and the sucrose in the chromatography column.

9. The method of claim 6, wherein the plurality of carbohydrates comprises a sucrose and a lactose, wherein the separating of the at least one of the plurality of carbohydrates comprises separating the sucrose and the lactose in the chromatography column.

10. The method of claim 6, wherein the first spacer comprises a linear and unsubstituted alkyl and the second spacer comprises an arylalkyl.

11. The method of claim 6, in which the first spacer comprises a first alkyl and the second spacer comprises a second alkyl, in which the first alkyl and the second alkyl are both a linear and unsubstituted alkyl.

12. The method of claim 6, in which the first spacer comprises a chemical formula of (—CH2—)x where x is from 3 to 10.

* * * * *